US008455690B2

(12) United States Patent
Takenaka et al.

(10) Patent No.: US 8,455,690 B2
(45) Date of Patent: Jun. 4, 2013

(54) METHOD FOR PRODUCING ARYLHYDROXYLAMINE

(75) Inventors: Yasumasa Takenaka, Tsukuba (JP); Jun-Chul Choi, Tsukuba (JP); Toshiyasu Sakakura, Tsukuba (JP); Hiroyuki Yasuda, Tsukuba (JP); Takahiro Kiyosu, Kawagoe (JP)

(73) Assignees: Wako Pure Chemical Industries, Ltd., Osaka-shi (JP); National Institute of Advanced Industrial Science and Technology, Tokyo (JP)

( * ) Notice: Subject to any disclaimer, the term of this patent is extended or adjusted under 35 U.S.C. 154(b) by 716 days.

(21) Appl. No.: 12/532,945

(22) PCT Filed: Mar. 27, 2008

(86) PCT No.: PCT/JP2008/055850
§ 371 (c)(1),
(2), (4) Date: Sep. 24, 2009

(87) PCT Pub. No.: WO2008/117844
PCT Pub. Date: Oct. 2, 2008

(65) Prior Publication Data
US 2010/0113830 A1 May 6, 2010

(30) Foreign Application Priority Data

Mar. 27, 2007 (JP) ................................. 2007-081040
Sep. 18, 2007 (JP) ................................. 2007-240585

(51) Int. Cl.
C07C 239/00 (2006.01)
(52) U.S. Cl.
USPC ........................................................ 564/300
(58) Field of Classification Search
USPC ........................................................ 564/300
See application file for complete search history.

(56) References Cited

U.S. PATENT DOCUMENTS

| 3,694,509 | A | | 9/1972 | Rylander et al. |
| 4,571,437 | A | * | 2/1986 | Caskey et al. .................. 564/418 |
| 4,723,030 | A | * | 2/1988 | Davis .............................. 560/19 |
| 5,166,435 | A | | 11/1992 | Sharma et al. |
| 5,288,906 | A | * | 2/1994 | Gubelmann et al. .......... 564/144 |
| 5,831,093 | A | * | 11/1998 | Gotz et al. ..................... 544/335 |
| 6,028,227 | A | * | 2/2000 | Chaudhari et al. ............. 564/418 |
| 6,031,106 | A | * | 2/2000 | Harreus et al. ................. 546/334 |
| 6,211,410 | B1 | | 4/2001 | Freudenreich et al. |
| 7,618,914 | B2 | * | 11/2009 | Sato et al. ..................... 502/159 |
| 2006/0106254 | A1 | * | 5/2006 | Sato et al. ..................... 564/300 |

FOREIGN PATENT DOCUMENTS

| JP | 54-024837 A | 2/1979 |
| JP | 60-139649 A | 7/1985 |
| WO | WO 99/28289 A1 | 6/1999 |
| WO | WO 2004/072019 A1 | 8/2004 |

OTHER PUBLICATIONS

Basu, S. et al. "MCM-41-supported platinum carbonyl cluster-derived catalysts for asymmetric and nonasymmetric hydrogenation reactions," J. Catalysis (2006) 239: 154-161.*
Pernoud, L. "Selective hydrogenation of nitrobenzene in[to] phenylhydroxylamine on silica supported platinum catalysts," Studies in Surf. Sci. Catal. (2000) 130: 2057-62.*
Holler, V. et al. "Three-phase nitrobenzene hydrogenation over supported glass fiber catalysts: Reaction kinetics study," Chem. Eng. Technol. (2000) 23: 251-5.*
Mandal, S. et al. "Pt and Pd nanoparticles immobilized on amine-functionalized zeolite: Excellent catalysts for hydrogenation and Heck reactions," Chem. Mater. (2004 16: 3714-24.*
Paul et al., *Journal of Organometallic Chemistry*, 689: 309-316 (2004).

* cited by examiner

*Primary Examiner* — Shailendra Kumar
(74) *Attorney, Agent, or Firm* — Leydig, Voit & Mayer, Ltd.

(57) ABSTRACT

The invention provides a method for producing an arylhydroxylamine compound efficiently and safely under mild conditions. The method involves contacting a nitroaryl compound with a hydrogen source in the presence of a platinum catalyst supported on amino group-coordinated silica and a poisoning agent.

11 Claims, 3 Drawing Sheets

METHOD FOR PRODUCING ARYLHYDROXYLAMINE

This application is a 371 of PCT/JP2008/055850, filed Mar. 27, 2008.

TECHNICAL FIELD

The present invention relates to a method for producing an arylhydroxylamine compound, which comprises contacting a nitroaryl compound with a hydrogen source in the coexistence of a platinum catalyst supported on amino group-coordinated silica and a poisoning agent.

BACKGROUND ART

An arylhydroxylamine compound is an extremely important compound as an intermediate such as, for example, polymerization inhibitors, antioxidants, agricultural chemicals, medicines, cosmetics and chemicals for an electronics industry.

As a method for producing an arylhydroxylamine compound, there are included, for example, (1) a method for subjecting a nitrobenzene and a hydrogen to a reaction, by using platinum-carbon (Pt/C) catalyst (see Patent Literature 1), (2) a method for reacting a nitrobenzene with hydrazine under reflux, in the presence of a platinum catalyst fixed on an ion exchange resin, (see to Patent Literature 2), and (3) a method for reacting a nitrobenzene with hydrogen gas, in the presence of a nitrogen base, a trivalent phosphorous compound and a hydrogenation catalyst (Pt/C) (see Patent Literature 3).

However, these methods have such problems that because of use of platinum-carbon, which is a combustible substance as a catalyst, sufficient caution is required in handling; progress of a reaction is delayed when hydrogen gas is used as a hydrogen source; because a reaction is performed under reflux, it is not preferable to be carried out in an industrial scale.

In addition, there is under investigation a method for producing an aniline in 100% conversion rate, by reacting a nitrobenzene with hydrogen gas, in the presence of a platinum carbonyl catalyst ($[Pt_{12}(CO)_{24}]^{2-}$) (a hydrogenation catalyst) supported on quaternary ammonium group-introduced silica (see Non-Patent Literature 1). However, this method has a problem that a substrate is reduced completely to aniline without stopping at a stage of N-phenylhydroxylamine.

Under these circumstances, it has been desired to develop a method for producing an arylhydroxylamine compound efficiently and safely under mild conditions.
[Patent Literature 1] U.S. Pat. No. 3,694,509
[Patent Literature 2] WO2004/072019
[Patent Literature 3] WO99/28289
[Non-Patent Literature 1] Journal of Organometallic Chemistry 689, (2004), p. 309-316

DISCLOSURE OF INVENTION

[Problem to be Solved by the Invention]

The present invention has been proposed in view of the above situation, and it is an object of the present invention to provide a method for producing an arylhydroxylamine compound efficiently and safely under mild conditions.

Problem to be Solved by the Invention

The present invention relates to a method for producing an arylhydroxylamine compound, which comprises contacting a nitroaryl compound with a hydrogen source in the coexistence of a platinum catalyst supported on amino group-coordinated silica and a poisoning agent.

That is, the present inventors have intensively studied a way to solve the above problems and found that by using a platinum catalyst supported on amino group-coordinated silica under specific condition, an arylhydroxylamine compound may be produced efficiently and safely under mild conditions, and have thus completed the present invention.
[Advantages of the Invention]

According to the method of the present invention, in which a nitroaryl compound is contacted with a hydrogen source in the coexistence of a platinum catalyst supported on amino group-coordinated silica and a poisoning agent, an arylhydroxylamine compound of an objective substance, may be produced efficiently, industrially and safely under mild conditions, without having the problems that a reaction must be carried out under severe condition such as under reflux; an expensive hydrogen source (e.g., hydrazine, etc.) is required; etc, which a conventional method had.

DESCRIPTION OF REFERENCE NUMERALS

In FIG. 1, FIG. 2, and FIGS. 6 to 8, —▲— represents result of remaining rate of nitorobenzene, —●— represents result of formation rate of N-phenylhydroxylamine, —◆— represents result of by-product rate of aniline (by-product), —□— represents result of conversion rate of nitrobenzene, and —○— represents result of selectivity of N-phenylhydroxylamine.

Figure 3:
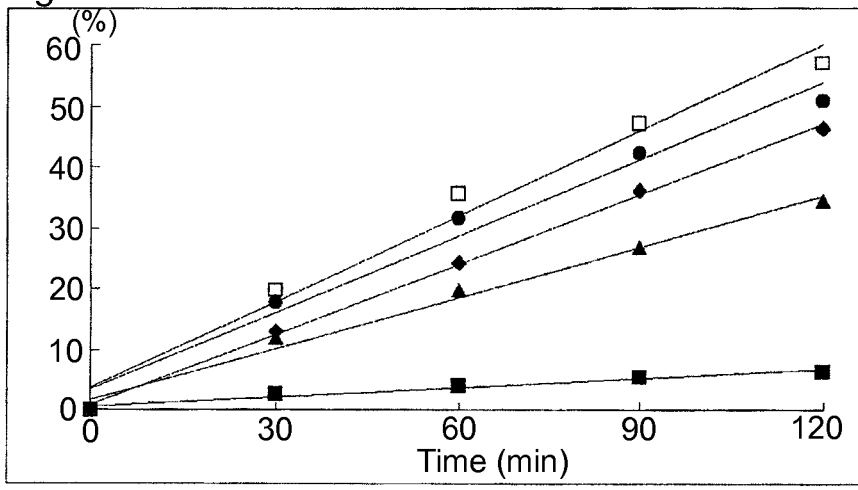
FIG. 3 shows formation rate of N-phenylhydroxylamine obtained in Comparative Example 4 and Examples 34 to 37.

In FIG. 3, —■— represents formation rate of N-phenylhydroxylamine obtained in Comparative Example 7; —▲— represents formation rate of N-phenylhydroxylamine obtained in Example 34; —♦— represents formation rate of N-phenylhydroxylamine obtained in Example 35; —●— represents formation rate of N-phenylhydroxylamine obtained in Example 36 by time course; and —□— represents formation rate of N-phenylhydroxylamine obtained in Example 37.

Figure 4:
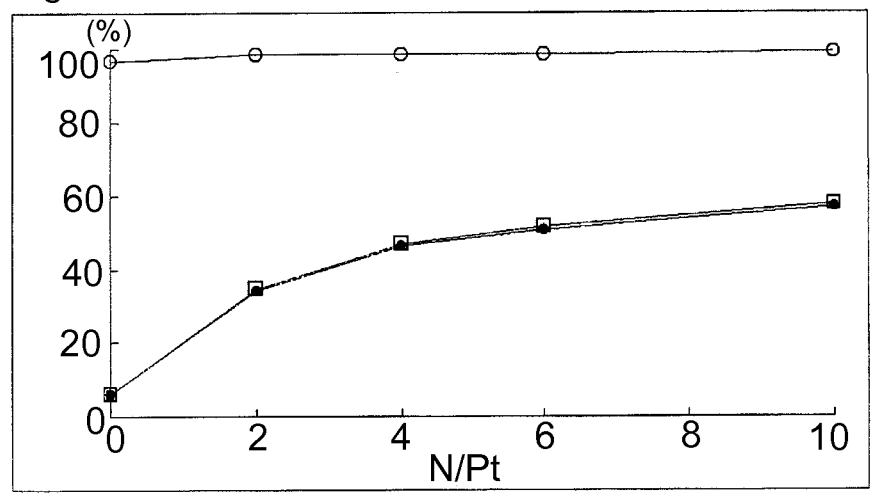
FIG. 4 shows formation rate of N-phenylhydroxylamine, conversion rate of nitorobenzene, and selectivity of N-phenylhydroxylamine, obtained in Comparative Example 7 and Examples 34 to 37, in the case of a reaction time of 120 minutes.
Figure 5:
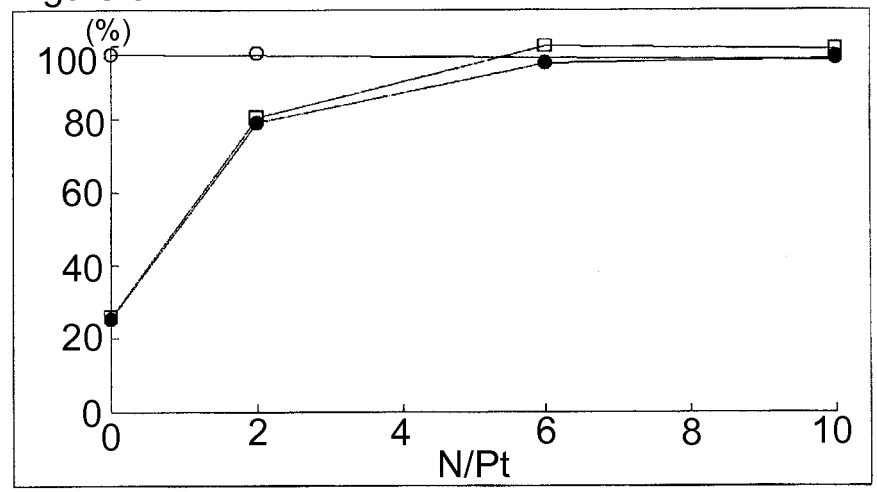
FIG. 5 shows formation rate of N-phenylhydroxylamine, conversion rate of nitorobenzene, and selectivity of N-phenylhydroxylamine, obtained in Comparative Example 8 and Examples 38 to 41, in the case of a reaction time of 120 minutes.

In FIG. 4 and FIG. 5, —●— represents formation rate of N-phenylhydroxylamine obtained in Comparative Examples 7 to 8 and Examples 34 to 41, in the case of a reaction time of 120 minutes; —□— represents conversion rate of nitrobenzene obtained in Comparative Examples 7 to 8 and Examples 34 to 41, in the case of a reaction time of 120 minutes; and —○— represents selectivity of N-phenylhydroxylamine obtained in Comparative Examples 7 to 8 and Examples 34 to 41, in the case of a reaction time of 120 minutes, respectively.

DETAILED DESCRIPTION OF THE INVENTION

The platinum catalyst supported on amino group-coordinated silica relevant to the method of the present invention (hereafter may be referred to as "the platinum catalyst supported on amino group-coordinated silica relevant to the present invention") is one exhibiting the specific catalytic action by giving the mutual influence of the relevant amino group, the relevant silica, and the relevant platinum in some way, and includes one in which the platinum catalyst supported on amino group-coordinated silica is obtained, for example, (1) by supporting a platinum on silica, which the amino group is introduced into (hereafter may be abbreviated as "amino group-containing silica"), (2) by contacting the platinum catalyst supported on silica with an amine compound corresponding to the relevant amino group, or (3) by supporting the relevant amine compound and platinum on silica at the same time.

Explanation will be given below in more specifically on these methods.

(1) The platinum catalyst supported on amino group-coordinated silica relevant to the present invention, obtained by supporting a platinum on amino group-containing silica (method 1)

As a method for supporting a platinum on amino group-containing silica, for example, there is a method for bonding a platinum-containing ion or a platinum complex, which is made present by dissolving of a platinum compound in a suitable solvent, to the amino group-containing silica, for example, by a complex formation reaction, a ligand exchange reaction or adsorption, and then subjecting it, if necessary, for example, to reduction treatment. Said catalyst obtained by this method has a state in which the platinum metal is fixed on the silica surface.

(2) The platinum catalyst supported on amino group-coordinated silica relevant to the present invention, obtained by contacting the platinum catalyst supported on silica with an amine compound corresponding to the relevant amino group (method 2)

As a method for contacting the platinum catalyst supported on silica with an amine compound corresponding to the relevant amino group, for example, there is a method for, by dissolving an amine compound into a suitable solvent, if necessary, and mixing the resultant solution and a platinum catalyst supported on silica, and removing the solvent thereafter.

In carrying out the production method of the present invention, in the case of using the catalyst prepared by the above method 2, the contacting of the relevant platinum catalyst supported on silica and the relevant amine compound may be carried out by mixing of these in advance, that is, after preparation in advance of the platinum catalyst supported on amino group-coordinated silica relevant to the present invention, in the presence of this and a poisoning agent, a nitroaryl compound and a hydrogen source may be reacted, however, the contacting of the relevant platinum catalyst supported on silica and the relevant amine compound by mixing, and the addition of the poisoning agent, the nitroaryl compound and the hydrogen source may be carried out at the same time.

(3) The platinum catalyst supported on amino group-coordinated silica obtained by supporting an amine compound corresponding to the relevant amino group and a platinum on silica, at the same time (method 3)

As a method for supporting the relevant amine compound and a platinum on silica, at the same time, for example, there is a method for subjecting a platinum-containing ion or a platinum complex, which is made present by dissolving of a platinum compound in a suitable solvent, and the relevant amine compound, to adsorption onto silica, and then subjecting it, if necessary, for example, to reduction treatment. The relevant catalyst obtained by this method has a state in which the platinum metal is fixed on the silica surface.

In addition, the adsorption of the relevant amine compound and platinum onto silica may be carried out by using, for example, a complex in which the relevant amine compound is coordinated onto platinum.

In carrying out the production method of the present invention, in the case of using the catalyst prepared by the above method 3, after supporting the relevant amine compound and platinum on silica, at the same time, by subjecting them to reducing treatment, the platinum catalyst supported on amino group-coordinated silica relevant to the present invention is prepared in advance, and then, in the presence of this and a poisoning agent, a nitroaryl compound and a hydrogen source may be reacted, however, the supporting of the relevant amine compound and platinum on silica, and the addition of the poisoning agent, the nitroaryl compound and the hydrogen source may be carried out at the same time.

Here, valence of a platinum atom in the platinum-containing ion or the platinum complex includes usually 0 to 6, and preferably 0, 2, 4 and 6.

To make the platinum-containing ion present in a suitable solvent, in obtaining the platinum catalyst supported on amino group-coordinated silica relevant to the present invention, a platinum compound to be dissolved in the relevant solvent includes, for example, platinum metal; platinum oxide such as $PtO_2$; a platinum halide such as platinum chloride, platinum bromide and platinum iodide; ammonium palatinate such as ammonium hexachloroplatinate and ammonium tetrachloroplatinate; potassium haloplatinate such as potassium hexachloroplatinate, potassium tetrachloroplatinate and potassium tetrabromoplatinate; sodium haloplatinate such as sodium hexachloroplatinate and sodium tetrachloroplatinate; platinum nitrate, platinum sulfate or platinum acetate. In particular, a potassium haloplatinate or a sodium haloplatinate is preferable, and among them, potassium tetrachloroplatinate or sodium tetrachloroplatinate is particularly preferable.

As the platinum complex, there is included, for example, a platinum complex coordinated with a ligand, and a specific example of the ligand includes, for example, 1,5-cyclooctadiene (COD), dibenzylideneacetone (DBA), norbornadiene (NBD), tricyclohexylphosphine (PCy$_3$), triethoxyphosphine (P(OEt)$_3$), tri-tert-butylphosphine (P(O$^t$Bu)$_3$), bipyridine (BPY), phenanthroline (PHE), triphenylphosphine (PPh$_3$), 1,2-bis(diphenylphosphino)ethane (DPPE), triphenoxyphosphine (P(OPh)$_3$), trimethoxyphosphine (P(OCH$_3$)$_3$), ethylene(CH$_2$=CH$_2$), ammonia(NH$_3$), N$_2$, NO or PO$_3$.

In obtaining the platinum catalyst supported on amino group-coordinated silica relevant to the present invention, a reaction solvent for dissolving the platinum compound includes, for example, water; alcohols having usually carbon atoms of 1 to 4, such as methanol, ethanol, propanol and butanol; ketones such as acetone and methylethyl ketone; esters such as ethyl acetate and butyl acetate; an organic solvent such as acetonitrile, dimethylformamide, tetrahydrofuran, chloroform dichloromethane and toluene, or a mixture thereof, among those, an organic solvent is preferable, and, in particular, tetrahydrofuran toluene is preferable. In addition, to make dissolution of the platinum compound easy, for example, an acid such as hydrochloric acid, sulfuric acid and nitric acid or a base such as sodium hydroxide and potassium hydroxide, may be added, as appropriate, to the relevant solvent.

A reduction treatment to be carried out in preparation of the platinum catalyst supported on amino group-coordinated silica relevant to the present invention, may be carried out by using a reducing agent usually used in this field, and the relevant reducing agent includes for example, hydrogen gas, hydrazine, sodium hydroborate, ammonium formate, diethylammonium formate, sodium hypophosphite, potassium hypophosphite or ethylene. Temperature of the reduction treatment is usually −20 to 500° C., preferably 0 to 400° C., and more preferably 10 to 300° C., and the reduction treatment method may be carried out according to a known method.

The platinum catalyst supported on amino group-coordinated silica relevant to the present invention, after preparation thereof, is identified with an X-ray photoelectron spectrometer or an X-ray absorption microstructure measurement apparatus, and is supposed that particles of a platinum metal are fixed (supported) at the surface of the silica.

In the platinum catalyst supported on amino group-coordinated silica relevant to the present invention, quantity of the platinum to be supported on the silica is usually 0.0001 to 50% by weight, preferably 0.01 to 20% by weight, and more preferably 0.01 to 15% by weight, as platinum weight, relative to total weight of the platinum catalyst supported on amino group-coordinated silica relevant to the present invention.

Silica (amino group-containing silica) introduced with an amino group, which is used to obtain the platinum catalyst supported on amino group-coordinated silica relevant to the method of the present invention, may be any one, in which the relevant amino group is bonded directly to silica, or in which it is bonded via a suitable linker, or in which an amine compound corresponding to the relevant amino group is adsorbed physically or chemically onto silica surface.

The amino group to be introduced onto the amino group-containing silica relevant to the present invention, as described above, includes, for example, amino groups such as primary amino group, secondary amino group, tertiary amino group and quaternary ammonium group, and among them, primary amino group, secondary amino group or tertiary amino group is preferable, and further, primary amino group or secondary amine are more preferable, primary amine is particularly preferable.

The secondary amino group includes, for example, a group represented by the general formula [1]:

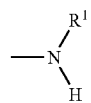

[1]

(wherein, R$^1$ represents alkyl group, aryl group, aralkyl group or hydroxyalkyl group), and the tertiary amino group includes, for example, a group represented by the following general formula [2]:

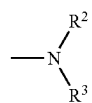

[2]

(wherein, R$^2$ and R$^3$ each independently represent alkyl group, aryl group, aralkyl group or hydroxyalkyl group. In addition, R$^2$ to R$^3$ and a nitrogen atom that they bond thereto may form a hetero ring), and the quaternary ammonium group includes, for example, a group represented by the following general formula [3]:

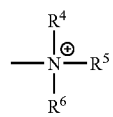

[3]

(wherein, R$^4$ to R$^6$ each independently represent alkyl group, aryl group, aralkyl group or hydroxyalkyl group. In addition, R$^4$ to R$^6$ and a nitrogen atom that they bond thereto may form a hetero ring).

In the above general formulae [1] to [3], the alkyl group represented by R$^1$ to R$^6$ may be any of straight chained, branched or ring-like, and includes one, for example, having carbon atoms of usually 1 to 12, preferably 1 to 6, more preferably 1 to 4, and still more preferably 1 or 2, and specifically, for example, there is included methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, n-hexyl group, isohexyl group, 3-methylpentyl group, 2-methylpentyl group, 1,2-dimethylbutyl group, n-heptyl group, isoheptyl group, sec-heptyl group, n-octyl group, isooctyl group, sec-octyl group, n-nonyl group, n-decyl group, n-undecyl group, n-dodecyl group, cyclopropyl group, cyclobutyl group, cyclopentyl group, cyclohexyl group, cycloheptyl group, cyclooctyl group, cyclononyl group, cyclodecyl group, cycloundecyl group or cyclododecyl group.

The aryl group represented by R$^1$ to R$^6$ represents one having carbon atoms of usually 6 to 10, and preferably 6, and specifically, includes for example, phenyl group, naphthyl group. These aryl groups may have, for example, usually 1 to 5, preferably 1 to 2 substituent groups such as alkyl group and hydroxyl group.

The alkyl group to be included as a substituent group of the above aryl group may be straight chained, branched or ring-like, and includes, for example, one having carbon atoms of usually 1 to 4, and preferably 1 to 2, and specifically, includes for example, methyl group, ethyl group, n-propyl group, isopropyl group, n-butyl group, isobutyl group, sec-butyl group, tert-butyl group, cyclopropyl group or cyclobutyl group.

The aralkyl group represented by $R^1$ to $R^6$ represents one having carbon atoms of usually 7 to 10, and specifically, includes for example, benzyl group, phenylethyl group, phenylpropyl group or phenylbutyl group.

The hydroxyalkyl group represented by $R^1$ to $R^6$ includes for example, one in which one of the hydrogen atoms of the alkyl group represented by the above $R^1$ to $R^6$ is substituted with a hydroxyl group, and one having carbon atoms of usually 1 to 12, preferably 1 to 6, more preferably 1 to 4, and still more preferably 1 or 2, and specifically includes for example, hydroxymethyl group, hydroxyethyl group, hydroxypropyl group, hydroxybutyl group, hydroxypentyl group, hydroxyhexyl group, hydroxyheptyl group, hydroxyoctyl group, hydroxynonyl group, hydroxydecyl group, hydroxyundecyl group, hydroxydodecylgroup, hydroxycyclopropyl group, hydroxycyclobutyl group, hydroxycyclopentyl group, hydroxycyclohexyl group, hydroxycycloheptyl group, hydroxycyclooctyl group, hydroxycyclononyl group, hydroxycyclodecyl group, hydroxycycloundecyl group or hydroxycyclododecyl group, among them, hydroxymethyl group and hydroxyethyl group are preferable, and hydroxyethyl group is particularly preferable.

In the general formulae [2] and [3], the hetero ring, which may be formed by $R^2$ to $R^3$ and a nitrogen atom that they bond thereto, along with the hetero ring, which may be formed by $R^4$ to $R^6$ and a nitrogen atom that they bond thereto, includes, for example, pyridine ring, pyrrole ring, pyrrolidine ring, pyrroline ring, piperidine ring, quinoline ring, indole ring, isoindoline ring or carbazole ring.

A specific example of the secondary amino group represented by the above general formula [1] includes, for example, an alkylamino group such as methylamino group, ethylamino group, n-propylamino group, isopropylamino group, n-butylamino group, isobutylamino group, sec-butylamino group, tert-butylamino group, n-pentylamino group, isopentylamino group, sec-pentylamino group, tert-pentylamino group, neopentylamino group, n-hexylamino group, isohexylamino group, sec-hexylamino group, tert-hexylamino group and neohexylamino group; an arylamino group such as phenylamino group; aralkylamino group such as benzylamino group; or a hydroxyalkylamino group such as hydroxymethylamino group, hydroxyethylamino group and hydroxypropylamino group.

A specific example of the tertiary amino group represented by the above general formula [2] includes, for example, a dialkylamino group such as dimethylamino group, ethylmethylamino group, diethylamino group and diisopropylamino group; or piperidinyl group.

A specific example of the quaternary ammonium group represented by the above general formula [3] includes, for example, a trialkylammonium group such as trimethylammonium group, triethylammonium group, triisopropylammonium group and n-heptylammonium group; a dialkylarylammonium group such as dimethylphenylammonium group; or pyridinyl group.

The quaternary ammonium group represented by the above general formula [3] is usually supplied in an ion-bonded state with a suitable anion. The anion, which forms ion bonding with the quaternary ammonium group includes, for example, a halide ion such as chloride ion, bromide ion, fluoride ion and iodide ion; hydroxide ion, sulfate ion or acetate ion, and among them, a chloride ion is preferable.

A linker to be used in bonding an amino group to silica via the linker, may include any one to be used usually in this field, and includes for example, alkylene group or arylene group.

The alkylene group to be included as the linker may be straight chained or branched, and includes one having carbon atoms of usually 1 to 12, preferably 1 to 6, and more preferably 1 to 3, and specifically includes, for example, a straight chained alkylene group such as methylene group, ethylene group, trimethylene group, tetramethylene group, pentamethylene group, hexamethylene group, heptamethylene group, octamethylene group, nonamethylene group, decamethylene group, undecamethylene group and dodecamethylene group; or a branched alkylene group such as ethylidene group, propylene group, isopropylidene group, ethylethylene group, 1-methyltrimethylene group, 2-methyltrimethylene group, 1-methyltetramethylene group, 2-methyltetramethylene group, 1-methylpentamethylene group, 2-methylpentamethylene group, 3-methylpentamethylene group, 3-methylhexamethylene group, 3-methylheptamethylene group, 3-methyloctamethylene group, 4-methylnonamethylene group and 3-ethyldecamethylene group, and among them, trimethylene group is preferable.

An arylene group to be included as the linker includes one having carbon atoms of usually 6 to 15, and specifically includes for example, phenylene group, naphthylene group or anthrylene group, and among them, p-phenylene group is preferable.

As a method for introducing an amino group to a silica, irrespective of the case where the amino group is directly introduced to the silica or the case where the amino group is introduced to the silica via the linker, a method to be used usually in this field may be used, as appropriate, and for example, it may be introduced by reacting an alkoxy site of a compound (e.g., dimethylaminopropyltrimethoxysilane, aminopropyltrimethoxysilane, etc.), in which the relevant amino group is introduced to a trialkoxysilane (e.g., trimethoxysilane, triethoxysilane, tripropoxysilane or tributoxysilane, etc.) having carbon atoms of 1 to 12, with silanol on the surface of silica.

In a method for preparing the above-described platinum catalyst supported on amino group-coordinated silica relevant to the present invention, as an amine compound to be used in making the amino group adsorb physically or chemically onto the silica surface (that is, in production of the amino group-containing silica), or as an amine compound to be used in a method for contacting the platinum catalyst supported on silica with the amine compound, and a method for supporting the amine compound and platinum on silica, at the same time, there is included an amine compound or an ammonium compound corresponding to the above primary amino group, the secondary amino group, the tertiary amino group and the quaternary ammonium group.

The amine compound to be used in a method for making the amine compound and platinum support on silica at the same time, there is included still more one to be coordinated on the silica surface and/or platinum in a bidentate state, by using a compound having 2 nitrogen atoms (diamines), such as bipyridines, phenanthrolines and alkylene diamines.

The primary amine compound corresponding to the primary amino group includes, for example, one represented by the general formula [8]:

$$R\text{---}NH_2 \qquad [8]$$

(wherein, R represents alkyl group, aryl group, aralkyl group or hydroxyalkyl group), and the secondary amine compound corresponding to the secondary amino group, includes, for example, one represented by the general formula [1']:

[1']

(wherein, R and $R^1$ are the same as the above), and the tertiary amine compound corresponding to the tertiary amino group, includes, for example, one represented by the general formula [2']:

[2']

(wherein, definitions of R, $R^2$ and $R^3$ are the same as the above). Still more, the quaternary ammonium compound (a quaternary ammonium salt) corresponding to the quaternary ammonium group, includes, for example, one represented by the general formula [3']:

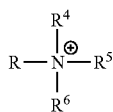

[3']

(wherein, definitions of R and $R^4$ to $R^6$ are the same as the above).

The quaternary ammonium compound represented by the above general formula [3'] is usually supplied in an ion-bonded state with a suitable anion. The anion which forms ion bonding with the quaternary ammonium compound includes, for example, a halide ion such as chloride ion, bromide ion, fluoride ion and iodide ion; hydroxide ion, sulfate ion or acetate ion, and among them, a chloride ion is preferable.

The bipyridines include, for example, those represented by the general formula [6]:

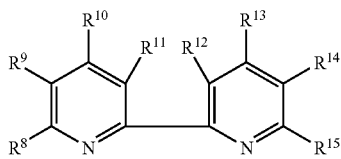

[6]

(wherein, $R^8$ to $R^{15}$ each independently represent hydrogen atom, carboxyl group, nitro group, hydroxyl group, alkyl group, alkoxy group, aryl group or alkylamino group).

The phenanthrolines include, for example, those represented by the general formula [7]:

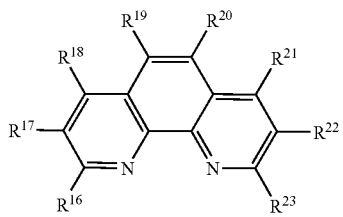

[7]

(wherein, $R^{16}$ to $R^{23}$ each independently represent hydrogen atom, carboxyl group, nitro group, hydroxyl group, alkyl group, alkoxy group, aryl group or alkylamino group).

The alkylenediamines includes, for example, those represented by the general formula [9]:

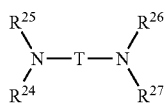

[9]

(wherein, $R^{24}$ to $R^{27}$ each independently represent hydrogen atom, alkyl group, aryl group or aralkyl group, and T represents an alkylene chain).

The alkyl group, aryl group, aralkyl group or hydroxyalkyl group represented by R in the general formulae [1'] to [3'] includes a similar one as in the exemplification of alkyl group, aryl group, aralkyl group or hydroxyalkyl group represented by $R^1$ to $R^6$, in the general formulae [1] to [3].

In the general formulae [6], [7] and [9], the alkyl group represented by $R^8$ to $R^{15}$ and $R^{16}$ to $R^{27}$ may be any of straight chained, branched or ring-like, and includes one having carbon atoms of usually 1 to 6, and specifically included, for example, methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, n-hexyl group, isohexyl group, 3-methylpentyl group, 2-methylpentyl group, 1,2-dimethylbutyl group, n-heptyl group, isoheptyl group, sec-heptyl group, n-octyl group, isooctyl group, sec-octyl group, n-nonyl group, n-decyl group, n-undecyl group, n-dodecyl group, cyclopropyl group, cyclobutyl group, cyclopentyl group, cyclohexyl group, cycloheptyl group, cyclooctyl group, cyclononyl group, cyclodecyl group, cycloundecyl group or cyclododecyl group.

In the general formulae [6] and [7], the alkoxy group represented by $R^8$ to $R^{15}$ and $R^{16}$ to $R^{23}$ may be straight chained, branched or ring-like, and includes one having carbon atoms of usually 1 to 6, and specifically includes, for example, methoxy group, ethoxy group, n-propoxy group, isopropoxy group, n-butoxy group, isobutoxy group, sec-butoxy group, tert-butoxy group, n-pentyloxy group, isopentyloxy group, sec-pentyloxy group, tert-pentyloxy group, neopentyloxy group, n-hexyloxy group, isohexyloxy group, 3-methylpentyloxy group, 2-methylpentyloxy group, 1,2-dimethylbutoxy group, n-heptyloxy group, isoheptyloxy group, sec-heptyloxy group, n-octyloxy group, isooctyloxy group, sec-octyloxy group, n-nonyloxy group, n-decyloxy group, n-undecyloxy group, n-dodecyloxy group, cyclopropoxy group, cyclobutoxy group, cyclopentyloxy group, cyclohexyloxy group, cycloheptyloxy group, cyclooctyloxy group, cyclononyloxy group, cyclodecyloxy group, cycloundecyloxy group or cyclododecyloxy group.

In the general formulae [6], [7] and [9], the aryl group represented by $R^8$ to $R^{15}$ and $R^{16}$ to $R^{23}$ includes one having carbon atoms of usually 6 to 10, and preferably 6, and specifically includes, for example, phenyl group or naphthyl group. These aryl groups may have usually 1 to 5, and preferably 1 to 2 substituent groups such as alkyl group and hydroxyl group.

In the general formulae [6] and [7], the alkylamino group represented by $R^8$ to $R^{15}$ and $R^{16}$ to $R^{23}$ includes one where a part of, or all of the hydrogen atoms of the amino group are substituted with an alkyl group, and the relevant alkyl group includes a similar one as in the exemplification of the alkyl group represented by the above $R^8$ to $R^{15}$ and $R^{16}$ to $R^{23}$.

In the general formula [9], the alkylene chain represented by T includes a straight chained one having carbon atoms of 1 to 6, and specifically includes, for example, methylene group, ethylene group, trimethylene group, tetramethylene group, pentamethylene group or hexamethylene group.

A typical specific example of the primary amine compound represented by the general formula [8] includes, for example, an alkyl amine such as methylamine, ethylamine, n-propylamine, isopropylamine, n-butylamine, isobutylamine, sec-butylamine, tert-butylamine, n-pentylamine, isopentylamine, sec-pentylamine, tert-pentylamine, neopentylamine, n-pentylamine, isopentylamine, tert-pentylamine, neopentylamine, n-hexylamine, isohexylamine, sec-hexylamine, tert-hexylamine and neohexylamine; an arylamine such as phenylamine; an aralkylamine such as benzylamine; a hydroxyalkylamine such as hydroxymethylamine, hydroxyethylamine and hydroxypropylamine, among them, alkylamine or aralkylamine is preferable.

A typical example of the secondary amine compound represented by the general formula [1'] includes a dialkyl amine such as dimethylamine, diethylamine and diisopropylamine; and for example, piperidine.

A typical specific example of the tertiary amine compound represented by the general formula [2'] includes, for example, a trialkylamine such as trimethylamine, triethylamine and triisopropylamine; dialkylarylamine such as dimethylphenylamine; or pyridine.

A typical specific example of the quaternary ammonium compound (quaternary ammonium salt) represented by the general formula [3'] includes, for example, a trialkylammonium salt such as trimethylammonium salt, triethylammonium salt and triisopropylammonium salt.

The bipyridines represented by the general formula [6] include, for example, 2,2'-bipyridine, 4,4'-dimethylbipyridine, 5,5'-dimethylbipyridine, 6,6'-dimethylbipyridine, 4,4'-di(tert-butyl)bipyridine, 5,5'-di(tert-butyl)bipyridine, 4,4'-diphenylbipyridine, 5,5'-diphenylbipyridine, 3,3'-dihydroxybipyridine, 4,4'-dihydroxybipyridine, 5,5'-dihydroxybipyridine, 3-hydroxybipyridine, 4,4'-dicarboxybipyridine, 5,5'-dicarboxybipyridine, 6,6'-dicarboxybipyridine, 4,4'-dinitrobipyridine, 5,5'-dinitrobipyridine, 6,6'-dinitrobipyridine, 4,4'-dimethoxybipyridine, 5,5'-dimethoxybipyridine, 6,6'-dimethoxybipyridine, 4,4'-dimethylaminobipyridine, 5,5'-dimethylaminobipyridine or 6,6'-dimethylaminobipyridine.

The phenanthrolines represented by the general formula [7] include, for example, 1,10-phenanthroline, 4,7-dimethyl-1,10-phenanthroline, 2,9-dimethyl-1,10-phenanthroline, 5,6-dimethyl-1,10-phenanthroline, 5,6-diphenyl-1,10-phenanthroline, 2,9-dimethyl-4,7-diphenyl-1,10-phenanthroline or 3,4,7,8-tetramethoxy-1,10-phenanthroline.

The alkylenediamines represented by the general formula [9] include, for example, N,N,N',N'-tetramethylethylenediamine (TMEDA) or N,N,N',N'-tetraethylethylenediamine.

Among bipyridines, phenanthrolines and alkylene diamines to be included as the diamines, alkylenediamines are preferable.

The amine compound to be used in preparation of the platinum catalyst supported on amino group-coordinated silica relevant to the present invention, includes primary amine compound, secondary amine compound, tertiary amine compound, quaternary ammonium salt or diamines, as described above, however, among these, primary amine compound, secondary amine compound and diamines are preferable, and primary amine compound is particularly preferable.

The platinum catalyst supported on silica to be used in obtaining the platinum catalyst supported on amino group-coordinated silica relevant to the present invention, includes one obtained by supporting a platinum on silica, and specifically, one obtained by subjecting a platinum-containing ion or a platinum complex, which is made present by dissolving of a platinum compound in a suitable solvent, to adsorption onto silica, and then subjecting it, if necessary, for example, to oxidation treatment, reduction treatment, etc. Said catalyst takes a state where the platinum metal is fixed on the silica surface.

The relevant platinum catalyst supported on silica may use a commercial product, or one synthesized, as appropriate, by a method commonly to be used in this field, for example, an impregnation method.

The silica relevant to the method of the present invention is porous silica commonly to be used as a carrier of this field, and specifically, there is included, for example, silica gel, mesoporous silica such as MCM-41 (which may be synthesized, for example, by a method described in C. T. Kresge, et. al., Nature 359, p 710 (1992)), SBA-15 (which may be synthesized, for example, by a method described in D. Zhao, et. al., Science 279, p. 548 (1998)), FSM-16 (which may be synthesized, for example, by a method described in S. Inagaki et. al., J. Chem. Soc. Chem. Commun., p. 680 (1993)), amorphous silica such as fumed silica, and porous glass, for example, crystalline silica such as silicalite. These porous silica may contain, a metal oxide such as alumina, magnesia and titania, as other component, as long as silica is a main component. In the relevant porous silica, silica gel and mesoporous silica are preferable, and among others, mesoporous silica is more preferable.

It is preferable that the relevant silica has suitable fine pores, and it is preferable that specific surface area of the relevant silica is present in a range so that the lower limit is usually equal to or larger than 10 $m^2/g$, and more preferably 50 $m^2/g$ and 100 $m^2/g$ in this order, while the upper limit is usually equal to or smaller than usually 2000 $m^2/g$, and more preferably 1500 $m^2/g$ and 1200 $m^2/g$ in this order.

In addition, pore volume of the relevant silica is, as the lower limit, usually equal to or larger than 0.01 $cm^3/g$, and more preferably 0.1 $cm^3/g$ and 0.3 $cm^3/g$, in this order, while as the upper limit, usually equal to or smaller than usually 10 $cm^3/g$, and more preferably 5 $cm^3/g$ and 3 $cm^3/g$ in this order.

It should be noted that values of these specific surface area and pore volume are obtained by measurement of a nitrogen adsorption and desorption isothermal line at a liquid nitrogen temperature of 77 K.

The silica relevant to the method of the present invention may be a synthesized one by a known method, or a commercial product.

A typical example of commercially available amorphous silica includes, for example, a CARiACT series (manufactured by Fuji Silysia Chem. Ltd.) such as CARiACT Q-3 (product name: with an average pore size of 3 nm), CARiACT Q-6 (product name: with an average pore size of 6 nm), CARiACT Q-10 (product name: with an average pore size of 10 nm), CARiACT Q-15 (product name: with an average pore size of 15 nm) and CARiACT Q-30 (product name: with an average pore size of 30 nm); Aerosil series (manufactured by Degussa Co., Ltd.) such as Aerosil (product name), Aerosil 300 (product name), Aerosil 380 (product name), Aerosil A300 (product name), Aerosil bs-50 (product name), Aerosil E300 (product name), Aerosil K7 (product name) and Aerosil M-300 (product name); Wakosil (manufactured by Wako Pure Chemical Industries, Ltd.) such as Wakosil C-200 (product name), Wakosil C-300 (product name); or Wako Gel (manufactured by Wako Pure Chemical Industries, Ltd.) such as Wako Gel C-100, Wako Gel C-200, Wako Gel C-300, Wako Gel C-300HG, Wako Gel C-400HG and Wako Gel C-500HG.

In the case where the platinum catalyst supported on silica is contacted with the amine compound, the contact may be performed in the absence of a solvent, or by using a reaction solvent. The reaction solvent includes, for example, water; organic solvents such as alcohols having carbon atoms of 1 to 4 including methanol, ethanol, propanol or butanol, ketones such as acetone or methylethyl ketone, esters such as ethyl acetate or butyl acetate, halogenated hydrocarbons such as chloroform or dichloromethane, acetonitrile, dimethylforamide, tetrahydrofuran and toluene; or mixtures thereof, and among these, an organic solvent is preferable, and particularly, tetrahydrofuran or propanol is preferable.

The amine compound to be contacted with the relevant platinum catalyst supported on silica includes a similar one as in the exemplification of the amine compound to be used in preparation of the amino group-containing silica relevant to the present invention.

In the case where the amine compound and platinum are subjected to supporting on silica at the same time, the relevant amine compound coordinated with a platinum complex may be used, and a specific example thereof includes, for example, $Py_2PtX_2$, $((CH_3)_2NCH_2)_2PtX_2$, $(H_3N)_2PtX_2$, $(EtN)_2PtX_2$ (wherein, Py represents pyridine, Et represents an ethyl group, X represents a halogen atom such as fluorine atom, chlorine atom, bromine atom and iodine atom) or bipyridylamine (bpy).

Explanation will be given below on a preparation method for the platinum catalyst supported on amino group-coordinated silica relevant to the present invention, with reference to specific examples.

<1> Preparation of the platinum catalyst supported on amino group-coordinated silica, obtained by supporting a platinum on the amino group-containing silica Explanation will be given below in more specifically on the preparation method for the platinum catalyst supported on amino group-coordinated silica relevant to the present invention, with reference to the case where mesoporous silica introduced with a dimethylaminopropyl group (which corresponds to the amino group relevant to the present invention, via a linker) was used.

(1) Preparation of the amino group-containing mesoporous silica (which corresponds to the amino group-containing silica relevant to the present invention)

Mesoporous silica and dimethylaminopropyltrimethoxy silane are subjected to a reaction in a suitable solvent (e.g., toluene, tetrahydrofuran, etc.), if necessary, under reflux. Subsequently, the resultant precipitate is filtered, washed and dried to obtain amino group-containing mesoporous silica introduced with a dimethylaminopropyl group.

(2) Preparation of a platinum catalyst supported on the amino group-coordinated and containing mesoporous silica (which corresponds to a platinum catalyst supported on the amino group-coordinated silica relevant to the present invention)

After the addition of a platinum compound, which enables to release an anion containing a platinum such as $K_2PtCl_4$, into a reaction solvent and the relevant amino group-containing mesoporous silica, said solution is subjected to a reaction. Subsequently, the resultant precipitate is filtered and washed, and subjected to reduction treatment with a suitable reducing agent to obtain the platinum catalyst supported on the amino group-coordinated mesoporous silica relevant to the present invention, where the platinum metal is fixed on the mesoporous silica.

As the reducing agent to be used in production of the above platinum catalyst supported on the amino group-coordinated silica, any one to be used generally as a reducing agent may be adopted, and a particularly preferable specific example includes, for example, hydrogen gas, hydrazine, sodium hydroborate, ammonium formate, diethylammonium formate, sodium hypophosphite, potassium hypophosphite or ethylene.

Temperature of the reduction treatment is usually −20 to 500° C., preferably 0 to 400° C., and more preferably 10 to 300° C., and the reduction treatment method may be carried out by a known method.

<2> Preparation of a platinum catalyst supported on the amino group-coordinated silica, obtained by contacting a platinum catalyst supported on silica with an amine compound, which corresponds to the relevant amino group After the addition of, for example, an amine compound such as triethylamine and a platinum catalyst supported on silica, if necessary, in a solvent such as propanol and tetrahydrofuran, and by stirring said solution, the platinum catalyst supported on the amino group-coordinated silica relevant to the present invention may be obtained.

In addition, in the production method of the present invention, synthesis of hydroxylamine to be described later, may be carried out, by the addition of a poisoning agent, a nitroaryl compound and a hydrogen source, at the same time of preparation of the catalyst relevant to the present invention.

<3> Preparation of a platinum catalyst supported on the amino group-coordinated silica, obtained by supporting an amine compound, which corresponds to the relevant amino group, and platinum on silica, at the same time After the addition of a platinum compound, which enables to release an anion containing a platinum such as $K_2PtCl_4$, and an amine compound into a reaction solvent together with silica, the relevant solution is subjected to stirring. Subsequently, the resultant precipitate is filtered and washed, and subjected to reduction treatment with, for example, a suitable reducing agent such as sodium hydroborate ($NaBH_4$) and hydrazine, to obtain the platinum catalyst supported on the amino group-coordinated silica relevant to the present invention.

In addition, in the production method of the present invention, synthesis of hydroxylamine to be described later, may be carried out, by the addition of a poisoning agent, a nitroaryl compound and a hydrogen source, at the same time of preparation of the catalyst relevant to the present invention.

An objective arylhydroxylamine compound may be obtained by contacting a nitroaryl compound with a hydrogen source, in the presence of the platinum catalyst supported on the amino group-coordinated silica obtained in this way and a poisoning agent.

The nitroaryl compound, in the method of the present invention includes, for example, a compound represented by the general formula [4]:

$$R^7\text{---}NO_2 \qquad [4]$$

(wherein, $R^7$ represents a hydrogen atom or an aryl group which may have a substituent group).

In the general formula [4], the aryl group of the aryl group which may have a substituent group represented by $R^7$ includes one having usually carbon atoms of 6 to 14, and preferably 6 to 10 includes, and specifically, for example, phenyl group, naphthyl group or anthryl group.

In addition, the aryl group represented by $R^7$ may have usually 1 to 10, preferably 1 to 5 and more preferably 1 to 3 substituent groups, and such a substituent group includes, for example, a straight chained, branched or ring-like alkyl group having carbon atoms of 1 to 6 such as methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, n-hexyl group, isohexyl group, cyclopropyl group, cyclobutyl group, cyclopentyl group and cyclohexyl group; a alkoxyl group having carbon atoms of 1 to 6 such as methoxy group, ethoxy group, n-propoxy group, butoxy group, pentyloxy group and hexyloxy group; an alkylsulfonylgroup having carbon atoms of 1 to 6 such as methylsulfonyl group, ethylsulfonyl group, propylsulfonyl group, butylsulfonyl group, pentylsulfonyl group and hexylsulfonylgroup; analkylthio group having carbon atoms of 1 to 6 such as methylthio group, ethylthio group, propylthio group, butylthio group, pentylthio group and hexylthio group; an acyl group having carbon atoms of 1 to 6 such as formyl group, acetyl group, propionyl group, butyryl group, valeryl group, pivaloyl group and hexanoyl group; an acyl group having carbon atoms of 1 to 6 such as formyloxy group, acetyloxy group, propionyloxy group, butyryloxy group, valeryloxy group, pivaloyloxy group and hexanoyloxy group; a halogen atom such as chlorine atom, bromine atom, fluorine atom and iodine atom; hydroxyl group, amino group, vinyl group, ethynyl group or cyano group.

Among a nitroaryl compound represented by the general formula [4] as above described, a nitrobenzene derivative such as nitrobenzene, nitrotoluene, nitroxylene, 4-fluoro-1-nitrobenzene, 4-chloro-1-nitrobenzene, 3-trifluoromethyl-1-nitrobenzene, 4-methyl-1-nitrobenzene and 4-methoxyl-1-nitrobenzene is preferable, and among them, nitrobenzene is particularly preferable.

The hydrogen source in the method of the present invention includes, for example, gas types such as hydrogen, carbon monoxide and ethylene; alcohols such as methanol, ethanol, isopropyl alcohol and butanol; hydrazines such as hydrazine, methylhydrazine, ethylhydrazine, tert-butylhydrazine, allylhydrazine and phenylhydrazine, and salts thereof (e.g., hydrochloride, sulfate, acetate, oxalate, etc.); carboxylic acids such as formic acid and acetic acid and salts thereof (e.g., alkaline salt such as sodium salt and potassium salt); hypophosphites such as sodium hypophosphite and potassium hypophosphite; ammonium formate, decalin or formaldehyde, and among these, gas types are preferable, and in particular, hydrogen gas is more preferable.

It should be noted that as the relevant hydrogen source, a hydrate or a substance in a state that moisture has been contained in advance may be used similarly.

In addition, it is one of the features of the present invention that the gas types such as hydrogen gas may be used as the hydrogen source.

Usage of the hydrogen source is usually 1 to 100 times mole, and preferably 1 to 50 times mole, relative to a nitroaryl compound, which is a reaction substrate of the method of the present invention, and in particular, usage of hydrogen gas, in the case where hydrogen gas is used as the hydrogen source, is usually 1 to 100 times mole, preferably 1 to 50 times mole, and more preferably 1 to 20 times mole, relative to the nitroaryl compound.

Usage of the platinum catalyst supported on amino group-coordinated silica relevant to the present invention is usually $1.0 \times 10^{-6}$ to 1 time mole, preferably $1.0 \times 10^{-4}$ to 0.5 time mole, and more preferably $1.0 \times 10^{-3}$ to 0.1 time mole, as quantity of platinum fixed, relative to the nitroaryl compound of the substrate.

The poisoning agent (generally called a catalyst poison substance) relevant to the method of the present invention, is one exhibiting a poisoning action against catalyst action of the platinum catalyst supported on amino group-coordinated silica relevant to the present invention, and includes any one which enables to still more enhance selectivity of arylhydroxylamine by the addition of the relevant poisoning agent.

The poisoning agent includes, for example, a compound, which contains an atom having an unshared electron pair (lone pair) such as oxygen atom and sulfur atom, phosphorus atom, heavy metal ion or halides, and specifically, for example, sulfoxides such as dimethylsulfoxide, diethylsulfoxide, tetramethylenesulfoxide and dibutylsulfoxide; sulfides such as diethylsulfide and methylphenylsulfide; phosphines such as triphenylphosphine, diphenyl(tert-butyl)phosphinomethane, diphenyl(tert-butyl)phosphinoethane and diphenyl(tert-butyl)phosphinopropane; phosphites, such as trimethyl phosphite, triethyl phosphite and triphenyl phosphate; a heavy metal ion such as mercury ion, arsenic ion, lead ion, bismuth ion and antimony ion; a halide such as sodium iodide and potassium iodide; carbon monoxide or carbon dioxide, and among them, for example, a compound, which contains an atom having an unshared electron pair (lone pair) such as oxygen atom, sulfur atom and phosphorus atom is preferable, and further, for example, sulfoxides or phosphines and the like are preferable, and dimethylsulfoxide is particularly preferable.

Usage of the poisoning agent is usually $1 \times 10^{-6}$ to $1 \times 10^{11}$ times mole, preferably $1 \times 10^{-3}$ to $1 \times 10^{-8}$ times mole, and more preferably 0.1 to $1 \times 10^{-5}$ times mole, relative to total quantity of platinum in a catalyst to be used.

In addition, in the method of the present invention, a reaction solvent is used, as appropriate, however, in the case where the nitroaryl compound or the hydrogen source or the like to be used is liquid, because they serve as a role of the solvent, further use of the reaction solvent is not necessary.

The reaction solvent includes, for example, water; organic solvents of alcohols such as methanol, ethanol, n-propanol, isopropanol, n-butanol, isobutanol, sec-butanol and tert-butanol; ketones such as acetone and methylethyl ketone; nitriles such as acetonitrile and butyronitrile; halogenated hydrocarbons such as dichloromethane, 1,2-dichloroethane, chloroform and carbon tetrachloride; ethers such as diethyl ether, dimethoxyethane, diethoxyethane and tetrahydrofuran; hydrocarbons such as n-hexane, n-heptane and cyclohexane; aromatic hydrocarbons such as benzene, toluene and xylene; esters such as ethyl acetate and butyl acetate, and among them, oxygen-containing organic solvents such as ethers, alcohols are preferable, and particularly, tetrahydrofuran or isopropanol is more preferable. They may be used alone or two or more kinds may be used in combination, as appropriate. In addition, according to the reaction solvent to be used or a combination thereof, reaction selectivity can be changed.

Usage of the reaction solvent is usually 1 to 50 times weight, preferably 1 to 20 times weight, and more preferably 1 to 10 times weight, relative to the nitroaryl compound, which is a reaction substrate.

Reaction temperature is usually −80 to 100° C., preferably −20 to 80° C., and more preferably 0 to 50° C.

Reaction time is usually 1 minute to 24 hours, preferably 5 minutes to 16 hours, and still more preferably 10 minutes to 12 hours.

Reaction pressure is usually 0.1 to 1 MPa, preferably 0.1 to 0.5 MPa, and more preferably 0.1 to 0.2 MPa That is, in order to obtain an arylhydroxylamine compound according to the method of the present invention, for example, a nitroaryl compound, which is a substrate, is mixed into about 1 to 50 times weight of a solvent, relative to said nitroaryl compound, and usually $1\times10^{-6}$ to $1\times10^{11}$ times mole of a poisoning agent, relative to total quantity of platinum in a catalyst to be used, and a platinum catalyst supported on amino group-coordinated silica relevant to the present invention is added thereto, so that $1.0\times10^{-6}$ to 1 time mole of platinum is present therein, relative to the nitroaryl compound, which is a substrate, and further 1 to 100 times mole of a hydrogen source such as hydrogen gas, is added, relative to the nitroaryl compound, which is a substrate, and then the resultant solution may be subjected to a reaction under stirring at room temperature for about 1 minute to 24 hours. After completion of the reaction, the relevant platinum catalyst supported on amino group-coordinated silica is removed by filtration, and the reaction solution is condensed and subjected, if necessary, to purification, as appropriate, according to a common procedure used in this field.

By the method of the present invention as described above, a nitro group of the nitroaryl compound represented by the above general formula [4] is converted to a hydroxyamino group to obtain the arylhydroxylamine compound represented by the corresponding general formula [5]:

$$R^7\text{—NHOH} \quad [5]$$

(wherein, $R^7$ is the same as the above.)

It should be noted that the method of the present invention can obtain an arylhydroxylamine compound represented by the general formula [5] as an objective substance in equivalent or higher yield as compared with the conventional method, without having such problems in the conventional method that a reaction must be carried out, for example, under severe condition under reflux condition and that use of an expensive raw material such as hydrazine is required as a hydrogen source.

In addition, the separation of the platinum catalyst supported on amino group-coordinated silica relevant to the present invention, used in the reaction, from the reaction solution after completion of the reaction, can use the catalyst as a catalyst for various reactions, without decrease in activity thereof repeatedly.

Explanation will be given below, in still more detail, on the present invention, with reference to Examples, however, the present invention should not be limited thereto.

EXAMPLES

Reference Example 1

Synthesis of dimethylaminopropyl Group-Containing silica

In a 200-mL flask, 2.5 g of mesoporous silica synthesized by a common procedure (e.g., Science, 1998, 279, 548-552, J. Am. Chem. Soc., 1998, 120, 6024-6036, etc.), 2.1 g of dimethylaminopropyltrimethoxysilane and 100 mL of toluene were subjected to a reaction for five days under reflux. After completion of the reaction, silica was filtered and then washed with dichloromethane, and subjected to drying under vacuum to obtain 3.3 g of dimethylaminopropyl group-containing silica.
[Property Data]
Specific surface area; 287 $m^2/g$
pore volume; 0.50 $cm^3/g$ Reference Example 2

Synthesis of aminopropyl Group-Containing silica

Similar operation as in Reference Example 1 is performed, except that 1.0 g of aminopropyltrimethoxysilane was used instead of dimethylaminopropyltrimethoxysilane, to obtain 3.0 g of aminopropyl group-containing silica.
[Property Data]
Specific surface area; 304 $m^2/g$
pore volume; 0.54 $cm^3/g$ Reference Example 3

Synthesis of dimethylaminopropyl Group-Containing silica (Q-10)

Similar operation as in Reference Example 1 is performed, except that 6.9 g of CARiACT-Q-10 (product name: manufactured by Fuji Silysia Chem. Ltd.), which is amorphous silica, was used instead of mesoporous silica of Reference Example 1, to obtain 8.5 g of dimethylaminopropyl group-containing silica (Q-10).
[Property Data]
Specific surface area; 212 $m^2/g$
pore volume; 1.00 $cm^3/g$ Reference Example 4

Synthesis of aminopropyl Group-Containing silica (Q-10)

Similar operation as in Reference Example 1 is performed, except that 6.9 g of CARiACT-Q-10 (product name: manufactured by Fuji Silysia Chem. Ltd.), which is amorphous silica, was used instead of mesoporous silica of Reference Example 1, to obtain 8.0 g of aminopropyl group-containing silica (Q-10).

Reference Example 5

Synthesis of dimethylaminopropyl Group-Containing silica (Q-6)

Similar operation as in Reference Example 1 is performed, except that 13.2 g of CARiACT-Q-6 (product name: manufactured by Fuji Silysia Chem. Ltd.), which is amorphous silica, was used instead of mesoporous silica of Reference Example 1, to obtain 15.0 g of aminopropyl group-containing silica (Q-6).
[Property Data]
Specific surface area; 405 m$^2$/g
pore volume; 0.53 cm$^3$/g Reference Example 6

Synthesis of Dimethylaminopropyl Group-Containing Silica (Q-3)

Similar operation as in Reference Example 1 is performed, except that 14.5 g of CARiACT-Q-3 (product name: manufactured by Fuji Silysia Chem. Ltd.), which is amorphous silica, was used instead of mesoporous silica of Reference Example 1, to obtain 17.7 g of aminopropyl group-containing silica (Q-3).
[Property Data]
Specific surface area; 419 m$^2$/g
pore volume; 0.27 cm$^3$/g Reference Example 7

Synthesis of the Platinum Catalyst Supported on amino Group-Coordinated silica Relevant to the Present Invention (1)

Into a 200-mL flask containing 2.0 g of the dimethylaminopropyl group-containing silica obtained in Reference Example 1 and 50 mL of water, 50 mL of an aqueous solution containing $12 \times 10^{-3}$ M of $K_2PtCl_4$ was added under stirring at room temperature, and a reaction was carried out under stirring at the same temperature for 7 days. After completion of the reaction, the silica was washed with water, and 50 mL of water and 25 mL of an aqueous solution containing 0.16 M of $NaBH_4$ were still more added at room temperature, and a reaction was carried out under stirring for 24 hours. After completion of the reaction, the silica was washed sequentially with water and ethanol, and subjected to drying under vacuum to obtain 2.1 g of the platinum catalyst supported on amino group-coordinated silica relevant to the present invention (1). Quantity of platinum supported on the resultant platinum catalyst supported on amino group-coordinated silica, determined by an ICP-AES method, was found to be about 8.9% by weight.

Reference Example 8

Synthesis of the Platinum Catalyst Supported on Amino Group-Coordinated Silica Relevant to the Present Invention (2)

Similar operation as in Reference Example 7 is performed, except that 1.2 g of the aminopropyl group-containing silica obtained in Reference Example 2 was used, instead of the dimethylaminopropyl group-containing silica obtained in Reference Example 1, to obtain 1.5 g of the platinum catalyst supported on amino group-coordinated silica relevant to the present invention (2). Quantity of platinum supported of the resultant platinum catalyst supported on amino group-coordinated silica, determined by an ICP-AES method, was found to be about 10.0% by weight.

Reference Example 9

Synthesis of the Platinum Catalyst Supported on Amino Group-Coordinated silica Relevant to the Present Invention (3)

Similar operation as in Reference Example 7 is performed, except that 2.0 g of the dimethylaminopropyl group-containing silica (Q-10) obtained in Reference Example 3 was used, instead of the dimethylaminopropyl group-containing silica obtained in Reference Example 1, to obtain 2.3 g of the platinum catalyst supported on amino group-coordinated silica relevant to the present invention (3). Quantity of platinum supported of the resultant platinum catalyst supported on amino group-coordinated silica, determined by an ICP-AES method, was found to be about 7.1% by weight.

Reference Example 10

Synthesis of the Platinum Catalyst Supported on Amino Group-Coordinated silica Relevant to the Present Invention (4)

Similar operation as in Reference Example 7 is performed, except that 3.3 g of the aminopropyl group-containing silica (Q-10) obtained in Reference Example 4 was used, instead of the dimethylaminopropyl group-containing silica obtained in Reference Example 1, to obtain 3.0 g of the platinum catalyst supported on amino group-coordinated silica relevant to the present invention (4). Quantity of platinum supported of the resultant platinum catalyst supported on amino group-coordinated silica, determined by an ICP-AES method, was found to be about 5.1% by weight.

Reference Example 11

Synthesis of the Platinum Catalyst Supported on Amino Group-Coordinated silica Relevant to the Present Invention (5)

Similar operation as in Reference Example 7 is performed, except that 2.0 g of the aminopropyl group-containing silica (Q-6) obtained in Reference Example 5 was used, instead of the dimethylaminopropyl group-containing silica obtained in Reference Example 1, to obtain 2.1 g of the platinum catalyst supported on amino group-coordinated silica relevant to the present invention (5). Quantity of platinum supported of the resultant platinum catalyst supported on amino group-coordinated silica, determined by an ICP-AES method, was found to be about 9.0% by weight.

Reference Example 12

Synthesis of the Platinum Catalyst Supported on Amino Group-Coordinated Silica Relevant to the Present Invention (6)

Similar operation as in Reference Example 7 is performed, except that 2.0 g of the aminopropyl group-containing silica (Q-3) obtained in Reference Example 6 was used, instead of the dimethylaminopropyl group-containing silica obtained in Reference Example 1, to obtain 2.4 g of the platinum catalyst supported on amino group-coordinated silica relevant to the present invention (6). Quantity of platinum supported of the resultant platinum catalyst supported on amino group-coordinated silica, determined by an ICP-AES method, was found to be about 8.5% by weight.

Example 1

Synthesis of arylhydroxylamine

Into a 25-mL flask, 11 mg (0.0025 time mole of platinum relative to nitrobenzene) of the platinum catalyst supported on amino group-coordinated silica (1) obtained in Reference Example 7, 2 mL of isopropyl alcohol (IPA), 30 µL of dimethylsulfoxide and 2 mmol of nitrobenzene were charged, and then a balloon sealed with hydrogen gas (about 2 L) was attached, and a reaction was carried out under stirring at room temperature for 12 hours under ordinary pressure. After completion of the reaction, 20 µL of the resultant reaction solution was diluted with 10 mL of 2-propanol containing 0.1 M of toluene, and after removal of the platinum catalyst supported on amino group-coordinated silica by using a membrane filter, an object was analyzed with High Performance Liquid Chromatography (HPLC) [wavelength: 236 nm, flow rate: 1 mL/min, mobile phase: a mixed solution of water/acetonitrile/acetic acid/triethylamine (=600/400/1/1), measurement time: 60 min, and standard substance: toluene], and as a result, conversion rate of nitrobenzene was 89.2% and yield of N-phenylhydroxylamine was 83.4% (selectivity 93.5%). The results are shown in Table 1.

It should be noted that selectivity here means % by mole of N-phenylhydroxylamine, in the case where reaction products (including by-products) formed by conversion of nitrobenzene is assumed as 100% by mole.

Examples 2 to 16

Similar operation as in Example 1 is performed, except that the platinum catalyst supported on amino group-coordinated silica (1) obtained in Reference Example 7, and dimethylsulfoxide (poisoning agent) were subjected to a reaction under condition of predetermined quantities and reaction times shown in Table 1, to obtain objects.

It should be noted that a substrate of Example 16 is 4-fluoro-1-nitrobenzene.

Results of HPLC analysis (Example 16 is $^1$H NMR analysis) are summarized altogether in Table 1.

TABLE 1

| | cat. | Pt quant. in Cat. (mol %) | Poisoning agent (µL) | Time (h) | Conversion rate (%) | Yield (%) | Selectivity (%) |
| --- | --- | --- | --- | --- | --- | --- | --- |
| Exam. 1 | Cat. (1) of Ref. Exam. 7 | 0.25 | 30 | 3 | 89.2 | 83.4 | 93.5 |
| Exam. 2 | Cat. (1) of Ref. Exam. 7 | 0.25 | 45 | 4 | 81.6 | 78.8 | 96.6 |
| Exam. 3 | Cat. (1) of Ref. Exam. 7 | 0.5 | 30 | 2 | 90.2 | 83.9 | 93 |
| Exam. 4 | Cat. (1) of Ref. Exam. 7 | 0.5 | 30 | 3 | 87.7 | 80.8 | 92.1 |
| Exam. 5 | Cat. (1) of Ref. Exam. 7 | 0.5 | 60 | 3 | 98.3 | 90.5 | 92.1 |
| Exam. 6 | Cat. (1) of Ref. Exam. 7 | 0.5 | 100 | 5 | >99.9 | 90.8 | 90.8 |
| Exam. 7 | Cat. (1) of Ref. Exam. 7 | 0.5 | 120 | 5 | >99.9 | 93 | 93 |
| Exam. 8 | Cat. (1) of Ref. Exam. 7 | 0.57 | 30 | 2 | 93.5 | 84.7 | 90.6 |
| Exam. 9 | Cat. (1) of Ref. Exam. 7 | 0.57 | 60 | 5 | >99.9 | 89.1 | 89.1 |
| Exam. 10 | Cat. (1) of Ref. Exam. 7 | 0.6 | 45 | 2 | 97.6 | 87 | 89.2 |
| Exam. 11 | Cat. (1) of Ref. Exam. 7 | 0.75 | 30 | 1 | 92.7 | 80.6 | 87 |
| Exam. 12 | Cat. (1) of Ref. Exam. 7 | 0.75 | 30 | 2 | >99.9 | 76.3 | 76.3 |
| Exam. 13 | Cat. (1) of Ref. Exam. 7 | 0.75 | 60 | 2 | 99.4 | 86.9 | 87.4 |
| Exam. 14 | Cat. (1) of Ref. Exam. 7 | 1 | 30 | 2 | 98.8 | 82.4 | 83.4 |
| Exam. 15 | Cat. (1) of Ref. Exam. 7 | 1 | 45 | 1 | 85.4 | 75.3 | 88.1 |
| Exam. 16 | Cat. (1) of Ref. Exam. 7 | 0.57 | 30 | 2 | >93.7 | 87.7 | 93.6 |

* substrate = 4-fluoro-1-nitrobenzene

Examples 17 to 26

Similar operation as in Example 1 is performed, except that various platinum catalysts supported on amino group-coordinated silica shown in Table 2, and dimethylsulfoxide (poisoning agent) were subjected to a reaction under condition of predetermined quantities and reaction times shown in Table 2, to obtain objects. Results of HPLC analysis are summarized altogether in Table 2.

TABLE 2

| | Cat. | Pt quant. in Cat. (mol %) | Poisoning agent (μL) | Time (h) | Conversion rate (%) | Yield (%) | Selectivity (%) |
|---|---|---|---|---|---|---|---|
| Exam. 17 | Cat. (2) of Ref. Exam. 8 | 0.5 | 30 | 2 | >99.9 | 66.1 | 66.1 |
| Exam. 18 | Cat. (2) of Ref. Exam. 8 | 0.64 | 30 | 2 | >99.9 | 60.2 | 60.2 |
| Exam. 19 | Cat. (2) of Ref. Exam. 8 | 0.64 | 60 | 5 | >99.9 | 66.1 | 66.1 |
| Exam. 20 | Cat. (3) of Ref. Exam. 9 | 0.5 | 30 | 2 | >99.9 | 58.7 | 58.7 |
| Exam. 21 | Cat. (3) of Ref. Exam. 9 | 0.45 | 60 | 5 | 95.2 | 71.7 | 75.3 |
| Exam. 22 | Cat. (4) of Ref. Exam. 10 | 0.32 | 60 | 5 | 89.5 | 74.6 | 83.4 |
| Exam. 23 | Cat. (4) of Ref. Exam. 10 | 0.5 | 30 | 2 | 99.2 | 65.3 | 65.9 |
| Exam. 24 | Cat. (5) of Ref. Exam. 11 | 0.5 | 30 | 2 | >99.9 | 69.4 | 69.4 |
| Exam. 25 | Cat. (5) of Ref. Exam. 11 | 0.5 | 30 | 2 | >99.9 | 75.7 | 75.7 |
| Exam. 26 | Cat. (6) of Ref. Exam. 12 | 0.5 | 30 | 2 | 98.7 | 86.3 | 87.4 |

Examples 27 to 33

Similar operation as in Example 1 is performed, except that a reaction was carried out under condition of predetermined reaction times using the predetermined amounts of the platinum catalysts supported on amino group-coordinated silica (1) obtained in Reference example 7 and various solvents and dimethylsulfoxide (poisoning agent), shown in Table 3, to obtain objects. Results of HPLC analysis are summarized altogether in Table 3.

TABLE 3

| | Cat. | Pt quant. in Cat. (mol %) | Solvent | Poisoning agent (μL) | Time (h) | Conversion rate (%) | Yield (%) | Selectivity (%) |
|---|---|---|---|---|---|---|---|---|
| Exam. 27 | Cat. (1) of Ref. Exam. 7 | 0.5 | THF | 30 | 6 | 61.3 | 60.7 | 99 |
| Exam. 28 | Cat. (1) of Ref. Exam. 7 | 0.5 | THF | 30 | 9 | 91.7 | 89.5 | 97.6 |
| Exam. 29 | Cat. (1) of Ref. Exam. 7 | 0.5 | THF | 30 | 12 | >99.9 | 93.4 | 93.4 |
| Exam. 30 | Cat. (1) of Ref. Exam. 7 | 0.5 | THF | 60 | 12 | 96.8 | 95.9 | 99.1 |
| Exam. 31 | Cat. (1) of Ref. Exam. 7 | 0.57 | EtOH | 30 | 2 | 98.5 | 82.1 | 83.4 |
| Exam. 32 | Cat. (1) of Ref. Exam. 7 | 0.57 | MtOH | 30 | 2 | 68.3 | 60.1 | 88 |

TABLE 3-continued

|  | Cat. | Pt quant. in Cat. (mol %) | Solvent | Poisoning agent (μL) | Time (h) | Conversion rate (%) | Yield (%) | Selectivity (%) |
|---|---|---|---|---|---|---|---|---|
| Exam. 33 | Cat. (1) of Ref. Exam. 7 | 0.57 | Bu$_2$O | 30 | 2 | 51.6 | 45.7 | 88.6 |

*THF = tetrahydrofuran, EtOH = ethanol, MeOH = methanol, Bu$_2$O = dibutyl ether Comparative Example 1

Into a 25-mL flask, 22 mg of the platinum catalyst supported on amino group-coordinated silica (1) obtained in Reference Example 7, 2 mL of 2-propanol, and 2 mmol of nitrobenzene were charged, and then a balloon sealed with hydrogen gas (about 2 L) was attached, and a reaction was carried out under stirring at room temperature for 2 hours. After completion of the reaction, an object was subjected to HPLC analysis under similar operation as in Example 1, and as a result, conversion rate of nitrobenzene was 99.9% or more and yield of N-phenylhydroxylamine was 0% (selectivity 0%).

Comparative Example 2

Into a 25-mL flask, 22 mg of the platinum catalyst supported on amino group-coordinated silica (1) obtained in Reference Example 7, 2 mL of tetrahydrofuran, and 2 mmol of nitrobenzene were charged, and then a balloon sealed with hydrogen gas (about 2 L) was attached, and a reaction was carried out under stirring at room temperature for 1 hour. After completion of the reaction, an object was subjected to HPLC analysis by similar operation as in Example 1, and as a result, conversion rate of nitrobenzene was 48.5% and yield of N-phenylhydroxylamine was 1.1% (selectivity 2.3%).

Comparative Example 3

Into a 25-mL flask, 39 mg of the silica gel platinum catalyst (5% by weight of Pt) [product name: 5% Pt-silica powder, manufactured by N. E. Chemcat Corp.], 2 mL of 2-propanol, 30 μL of dimethylsulfoxide, and 2 mmol of nitrobenzene were charged, and then a balloon sealed with hydrogen gas (about 2 L) was attached, and a reaction was carried out under stirring at room temperature for 2 hours. After completion of the reaction, an object was subjected to HPLC analysis by similar operation as in Example 1, and as a result, conversion rate of nitrobenzene was 15.6% and yield of N-phenylhydroxylamine was 15.2% (selectivity 97.6%).

Still more, as a result of performing of the reaction under similar conditions as above by setting reaction time at 20 hours, it has been found that conversion rate of nitrobenzene was 44.7%, and yield of N-phenylhydroxylamine was 24.1% (selectivity 53.9%).

Comparative Example 4

(1) Synthesis of a Platinum Catalyst Supported on mesoporous silica

Onto 2.0 g of mesoporous silica synthesized by a common procedure (e.g., Science, 1998, 279, 548-552, J. Am. Chem. Soc., 1998, 120, 6024-6036, etc.), 6.44 mL of an aqueous solution containing $2.9 \times 10^{-2}$ M of H$_2$PtCl$_6$ hexahydrate were dropped, and after standing still at room temperature for 2 hours, the solution was dried under vacuum at 60° C. for 1.5 hour. Still more, the resultant dried substance was calcinated at 500° C. for 4 hours to obtain 2.0 g of the platinum catalyst supported on mesoporous silica. Quantity of platinum supported on the resultant relevant platinum catalyst supported on mesoporous silica was found to be about 1.79% by weight, by calculation result from total platinum quantity used.

(2) Synthesis of arylhydroxylamine

Into a 25-mL flask, 20 mg of the platinum catalyst supported on mesoporous silica obtained in the above (1) of Comparative Example 4, 2 mL of 2-propanol, 30 μl, of dimethylsulfoxide, and 2 mmol of nitrobenzene were charged, and then a balloon sealed with hydrogen gas (about 2 L) was attached, and a reaction was carried out under stirring at room temperature for 2 hours. After completion of the reaction, an object was subjected to HPLC analysis by similar operation as in Example 1, and as a result, conversion rate of nitrobenzene was 0.1% and yield of N-phenylhydroxylamine was 0.25% (selectivity 100%).

Comparative Example 5

A Method for Producing an arylhydroxylamine Using a Platinum Catalyst Supported on silica Into a 25-mL flask, 39 mg of the silica gel platinum catalyst (5% by weight of Pt) [product name: 5% Pt-silica powder, manufactured by N. E. Chemcat Corp.] (0.0026 time mole of platinum, relative to nitrobenzene), 2 mL of isopropyl alcohol (IPA), and 2 mmol of nitrobenzene were charged, and then a balloon sealed with hydrogen gas (about 2 L) was attached, and a reaction was carried out under stirring at room temperature for each of the predetermined times (15 minutes, 30 minutes, 45 minutes, 60 minutes, 75 minutes, 90 minutes, 105 minutes and 120 minutes) under ordinary pressure. After completion of the reaction, 20 μL of the resultant reaction solution was diluted with 10 mL of 2-propanol containing 0.1 M of toluene, and after removal of the catalyst by using a membrane filter, an object was analyzed with High Performance Liquid Chromatography (HPLC) [wavelength: 236 nm, flow rate: 1 mL/min, mobile phase: a mixed solvent of water/acetonitrile/acetic acid/triethylamine (=600/400/1/1), measurement time: 60 min, and standard substance: toluene].

Figure 1:
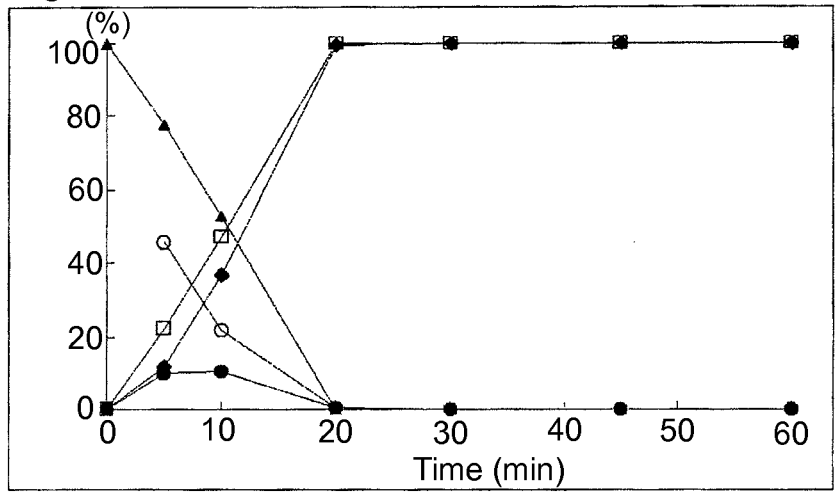
FIG. 1 shows remaining rate of nitorobenzene, formation rate of N-phenylhydroxylamine, by-product rate of aniline (by-product), conversion rate of nitorobenzene, and yield of N-phenylhydroxylamine, obtained in Comparative Example 5.

Remaining rate of nitorobenzene, formation rate of N-phenylhydroxylamine, by-product rate of anilne (by-product), conversion rate of nitrobenzene, and yield of N-phenylhydroxylamine, in the time course by each 15 minutes of the reaction time, are summarized altogether in FIG. 1.

It should be noted that each line in FIG. 1 shows the following item:

—▲— line: remaining rate of nitorobenzene
—●— line: formation rate of N-phenylhydroxylamine,
—◆— line: by-product rate of aniline (by-product),
—□— line: conversion rate of nitrobenzene
—○— line: selectivity of N-phenylhydroxylamine

Comparative Example 6

A Method for Producing an Arylhydroxylamine Using a Platinum Catalyst Supported on Silica Into a 25-mL flask, 39 mg of the silica gel platinum catalyst (5% by weight of Pt) [product name: 5% Pt-silica powder, manufactured by N. E. Chemcat Corp.] (0.0026 time mole of platinum, relative to nitrobenzene), 2 mL of isopropyl alcohol (IPA), 0.007 mmol of triethylamine (10 equivalents, relative to platinum weight in the silica gel platinum catalyst) and 2 mmol of nitrobenzene were charged, and then a balloon sealed with hydrogen gas (about 2 L) was attached, and a reaction was carried out under stirring at room temperature for each of the predetermined times (15 minutes, 30 minutes, 45 minutes, 60 minutes, 75 minutes, 90 minutes, 105 minutes, and 120 minutes) under ordinary pressure. After completion of the reaction, 20 μL of the resultant reaction solution was diluted with 10 mL of 2-propanol containing 0.1 M of toluene, and after removal of the catalyst by using a membrane filter, an object was analyzed with High Performance Liquid Chromatography (HPLC) [wavelength: 236 nm, flow rate: 1 mL/min, mobile phase: a mixed solvent of water/acetonitrile/acetic acid/triethylamine (=600/400/1/1), measurement time: 60 min, and standard substance: toluene].

Figure 2:
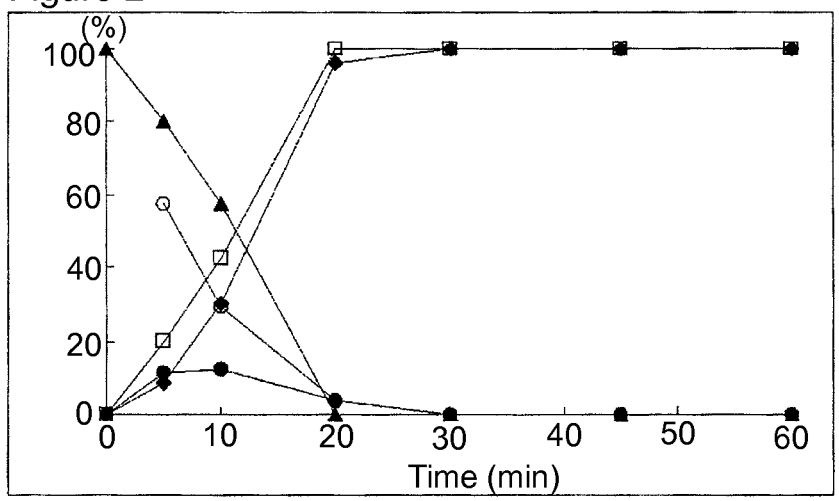
FIG. 2 shows remaining rate of nitorobenzene, formation rate of N-phenylhydroxylamine, by-product rate of aniline (a by-product), conversion rate of nitorobenzene, and yield of N-phenylhydroxylamine, obtained in Comparative Example 6.

Remaining rate of nitrobenzene, formation rate of N-phenylhydroxylamine, by-product rate of anilne (by-product), conversion rate of nitrobenzene, and yield of N-phenylhydroxylamine, in the time course by each 15 minutes of the reaction time, are summarized altogether in FIG. 2.

It should be noted that each line in FIG. 2 shows the following item:

—▲— line: remaining rate of nitrobenzene
—●— line: formation rate of N-phenylhydroxylamine,
—♦— line: by-product rate of aniline (a by-product),
—□— line: conversion rate of nitrobenzene
—○— line: selectivity of N-phenylhydroxylamine

Examples 34 to 37

A Method for Producing an Arylhydroxylamine Using a Platinum Catalyst Supported on Silica Into a 25-mL flask, 39 mg of the silica gel platinum catalyst (5% by weight of Pt) [product name: 5% Pt-silica powder, manufactured by N. E. Chemcat Corp.] (0.0026 time mole of platinum, relative to nitrobenzene), 2 mL of isopropyl alcohol (IPA), 30 μL of dimethylhydroxylamine, each predetermined quantity of triethylamine (2 equivalents, 4 equivalents, 6 equivalents, and 10 equivalents, relative to platinum weight (N/Pt) in the silica gel platinum catalyst) and 2 mmol of nitrobenzene were charged, and then a balloon sealed with hydrogen gas (about 2 L) was attached, and a reaction was carried out under stirring at room temperature for each of the predetermined times (30 minutes, 60 minutes, 90 minutes, and 120 minutes) under ordinary pressure. After completion of the reaction, 20 μL of the resultant reaction solution was diluted with 10 mL of 2-propanol containing 0.1 M of toluene, and after removal of the platinum catalyst supported on silica by using a membrane filter, an object was analyzed with High Performance Liquid Chromatography (HPLC) [wavelength: 236 nm, flow rate: 1 mL/min, mobile phase: a mixed solvent of water/acetonitrile/acetic acid/triethylamine (=600/400/1/1), measurement time: 60 min, and standard substance: toluene].

Formation rates of N-phenylhydroxylamine (%) by time course are shown in FIG. 3. In addition, conversion rate of nitrobenzene (%), and selectivity of N-phenylhydroxylamine (%), in the case of a reaction time of 120 minutes are shown in FIG. 4.

Comparative Example 7

A Method for Producing an Arylhydroxylamine Using a Platinum Catalyst Supported on Silica Similar operation as in Examples 34 to 37 is performed, except that triethylamine was not added, to obtain an object.

Formation rates of N-phenylhydroxylamine (%) by time course are summarized in FIG. 3. In addition, conversion rate of nitrobenzene (%), and selectivity of N-phenylhydroxylamine (%), in the case of a reaction time of 120 minutes are summarized altogether in FIG. 4.

It should be noted that each line in FIG. 3 shows the following item:

—■— line: formation rate of N-phenylhydroxylamine obtained by Comparative Example 7 (N/Pt=0)
—▲— line: formation rate of N-phenylhydroxylamine obtained by Example 34 (N/Pt=2)
—♦— line: formation rate of N-phenylhydroxylamine obtained by Example 35 (N/Pt=4)
—●— line: formation rate of N-phenylhydroxylamine obtained by Example 36 (N/Pt=6)
—□— line: formation rate of N-phenylhydroxylamine obtained by Example 37 (N/Pt=10)

It should be noted that each line in FIG. 4 shows the following item:

—●— line: formation rate of N-phenylhydroxylamine in the case of the reaction time of 120 minutes, obtained in Comparative Example 7 and Examples 34 to 37
—□— line: conversion rate of nitrobenzene in the case of the reaction time of 120 minutes, obtained in Comparative Example 7 and Examples 34 to 37
—○— line: selectivity of N-phenylhydroxylamine in the case of the reaction time of 120 minutes, obtained in Comparative Example 7 and Examples 34 to 37

Examples 38 to 41

A Method for Producing an Arylhydroxylamine Using a Platinum Catalyst Supported on Silica Similar operation as in Example 34 is performed, except that 39 mg of the silica gel platinum catalyst (5% by weight of Pt) [product name: 5% Pt-silica powder, manufactured by N. E. Chemcat Corp.] (0.010 time mole of platinum, relative to nitrobenzene), and each predetermined quantity of triethylamine (2 equivalents, 4 equivalents, 6 equivalents, and 10 equivalents, relative to platinum weight (N/Pt) in the silica gel platinum catalyst) were used and a reaction was performed for each of the predetermined times (60 minutes, 90 minutes and 120 minutes), to obtain an object.

Conversion rate of nitrobenzene (%) and selectivity of N-phenylhydroxylamine (%), in the case of a reaction time of 120 minutes, are summarized in FIG. 5. In addition, results of Examples 40 and 41 are shown in Table 4.

TABLE 4

|  | Reaction time | Triethylamine (N/Pt) | Conversion rate of nitrobenzene-5 | Selectivity of N-phenylhydroxylamine (%) |
|---|---|---|---|---|
| Example 40 | 60 minutes | 6 equivalents | 100 | 95.2 |
|  | 90 minutes |  | 100 | 91.9 |
|  | 120 minutes |  | 100 | 89.3 |
| Example 41 | 60 minutes | 10 equivalents | 99.2 | 97.3 |
|  | 90 minutes |  | 100 | 95.5 |
|  | 120 minutes |  | 100 | 93.6 |
|  | 150 minutes |  | 100 | 92.2 |

Comparative Example 8

A Method for Producing an Arylhydroxylamine Using a Platinum Catalyst Supported on Silica Similar operation as in Examples 38 to 41 is performed, except that triethylamine was not added, to obtain an object.

Conversion rate of nitorobenzene (%) and selectivity of N-phenylhydroxylamine (%), in the case of a reaction time of 120 minutes, are summarized altogether in FIG. 5.

It should be noted that each line in FIG. 5 shows the following item:

—●— line: formation rate of N-phenylhydroxylamine in the case of the reaction time of 120 minutes, obtained in Comparative Example 8 and Examples 38 to 41

—□— line: conversion rate of nitorobenzene in the case of the reaction time of 120 minutes, obtained in Comparative Example 8 and Examples 38 to 41

—○— line: selectivity of N-phenylhydroxylamine in the case of the reaction time of 120 minutes, obtained in Comparative Example 8 and Examples 38 to 41

Reference Example 13

Synthesis of the Platinum Catalyst Supported on Amino Group-Coordinated Silica Relevant to the Present Invention Into a 100-mL flask containing 1.3 g of the dimethylaminopropyl group-containing silica obtained in Reference Example 1, and 50 mL of water, 20 mL of an aqueous solution containing $2.0 \times 10^{-2}$ M of $K_2PtCl_4$ was added under stirring at room temperature, and a reaction was carried out under stirring at the same temperature for 24 hours. After completion of the reaction, the silica was washed with water, and 50 mL of water and 25 mL of an aqueous solution containing 0.16 M of $NaBH_4$ were still more added at room temperature and a reaction was carried out under stirring for 24 hours. After completion of the reaction, the silica was washed sequentially with water and ethanol, and subjected to drying under vacuum to obtain 1.40 g of the platinum catalyst supported on amino group-coordinated silica relevant to the present invention (1). Quantity of platinum supported on the resultant platinum catalyst supported on amino group-coordinated silica, determined by an ICP-AES method, was found to be about 5.10% by weight.

Example 42

A Method for Producing an Arylhydroxylamine Using the Platinum Catalyst Supported on Amino Group-Coordinated Silica Relevant to the Present Invention Into a 25-mL flask, 20 mg (0.0029 time mole of platinum, relative to nitrobenzene) of the platinum catalyst supported on amino group-coordinated silica obtained in Reference Example 13, 2 mL of isopropyl alcohol (IPA), 30 μL of dimethylsulfoxide and 2 mmol of nitrobenzene were charged, and then a balloon sealed with hydrogen gas (about 2 L) was attached, and a reaction was carried out under stirring at room temperature for each of the predetermined times (30 minutes, 60 minutes, 90 minutes, 120 minutes, 150 minutes and 180 minutes) under ordinary pressure. After completion of the reaction, 20 μL of the resultant reaction solution was diluted with 10 mL of 2-propanol containing 0.1 M of toluene, and after removal of the platinum catalyst supported on amino group-coordinated silica by using a membrane filter, an object was analyzed with High Performance Liquid Chromatography (HPLC) [wavelength: 236 nm, flow rate: 1 mL/min, mobile phase: a mixed solvent of water/acetonitrile/acetic acid/triethylamine (=600/400/1/1), measurement time: 60 min, and standard substance: toluene].

Figure 6:
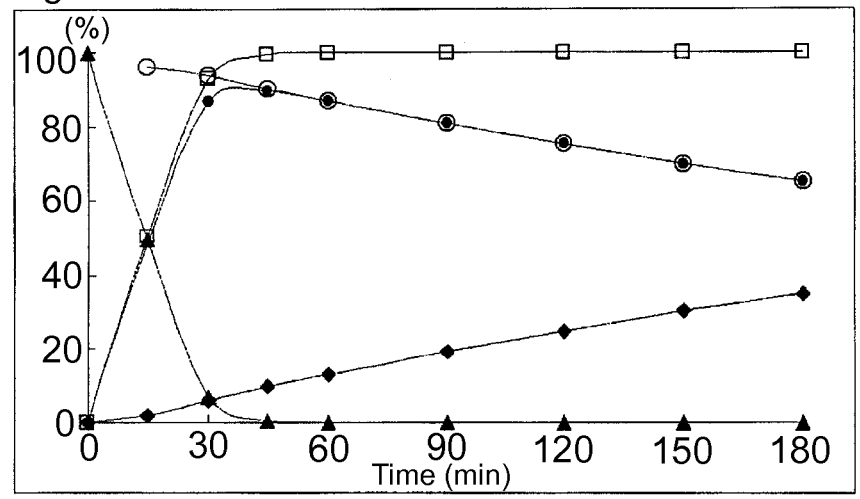
FIG. 6 shows remaining rate of nitorobenzene, formation rate of N-phenylhydroxylamine, by-product rate of aniline (by-product), conversion rate of nitorobenzene, and yield of N-phenylhydroxylamine, obtained in Example 40.

Remaining rate of nitorobenzene, formation rate of N-phenylhydroxylamine, by-product rate of anilne (by-product), conversion rate of nitorobenzene, and yield of N-phenylhydroxylamine, in the time course, are summarized altogether in FIG. 6.

It should be noted that each line in FIG. 6 shows the following item:
—▲— line: remaining rate of nitrobenzene
—●— line: formation rate of N-phenylhydroxylamine,
—♦— line: by-product rate of aniline (by-product),
—□— line: conversion rate of nitrobenzene
—○— line: selectivity of N-phenylhydroxylamine Reference Example 14

Synthesis of the Platinum Catalyst Supported on Amino Group-Coordinated Silica Relevant to the Present Invention Into a 100-mL flask containing 1.3 g of the dimethylaminopropyl group-containing silica obtained in Reference Example 1 and 50 mL of water, 20 mL of an aqueous solution containing 4.1×10$^{-2}$ M of K$_2$PtCl$_4$ was added under stirring at room temperature, a reaction was carried out under stirring at the same temperature for 24 hours. After completion of the reaction, the silica was washed with water, and 50 mL of water and 25 mL of an aqueous solution containing 0.16 M of NaBH$_4$ was still more added at room temperature and a reaction was carried out under stirring for 24 hours. After completion of the reaction, the silica was washed sequentially with water and ethanol, and subjected to drying under vacuum to obtain 1.52 g of the platinum catalyst supported on amino group-coordinated silica relevant to the present invention (1). Quantity of platinum supported on the resultant platinum catalyst supported on amino group-coordinated silica, determined by an ICP-AES method, was found to be about 9.73% by weight.

Example 43

A Method for Producing an Arylhydroxylamine Using the Platinum Catalyst Supported on Amino Group-Coordinated Silica Relevant to the Present Invention Similar operation as in Example 42 is performed, except that 20 mg of the platinum catalyst supported on amino group-coordinated silica (0.0050 time mole of platinum, relative to nitrobenzene) obtained in Reference Example 14, was used, and a reaction was performed for each of the predetermined times (30 minutes, 60 minutes, 90 minutes and 120 minutes), to obtain an object.

Figure 7:
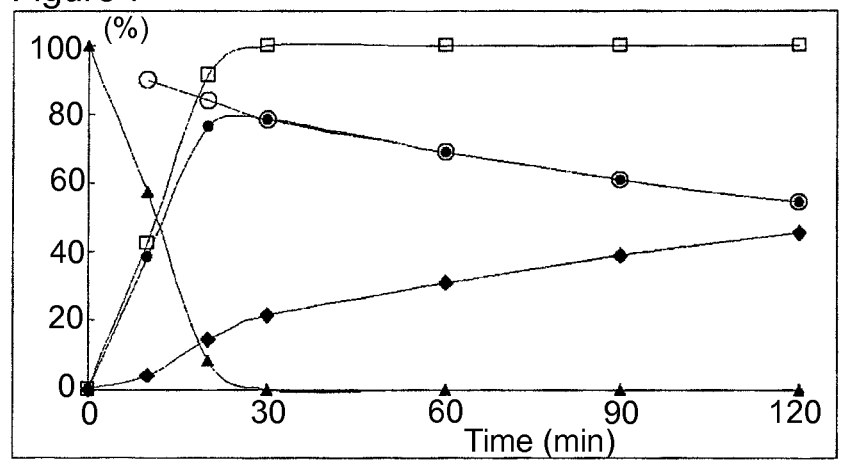
FIG. 7 shows remaining rate of nitorobenzene, formation rate of N-phenylhydroxylamine, by-product rate of aniline (a by-product), conversion rate of nitorobenzene, and yield of N-phenylhydroxylamine, obtained in Example 41.

Remaining rate of nitrobenzene, formation rate of N-phenylhydroxylamine, by-product rate of anilne (by-product), conversion rate of nitrobenzene, and yield of N-phenylhydroxylamine, in the time course, are summarized altogether in FIG. 7.

It should be noted that each line in FIG. 7 shows the following item:
—▲— line: remaining rate of nitrobenzene
—●— line: formation rate of N-phenylhydroxylamine,
—♦— line: by-product rate of aniline (a by-product),
—□— line: conversion rate of nitrobenzene
—○— line: selectivity of N-phenylhydroxylamine Example 44

A Method for Producing an Arylhydroxylamine Using a Platinum Catalyst Supported on Silica Into a flask, 20 mg of the silica gel platinum catalyst (5% by weight of Pt) [product name: 5% Pt-silica powder "Escat™ 2351", manufactured by STREM Co., Ltd.] (0.0026 time mole of platinum, relative to nitrobenzene), 2 mL of IPA, 30 µL of dimethylsulfoxide, 10 µL of triethylamine (14 equivalents, relative to platinum weight (N/Pt) in the silica gel platinum catalyst) and 2 mmol of nitrobenzene were charged, and then a balloon sealed with hydrogen gas (about 2 L) was attached, and a reaction was carried out under stirring at room temperature for 2 hours under ordinary pressure. After completion of the reaction, 20 µL of the resultant reaction solution was diluted with 10 mL of 2-propanol containing 0.1 M of toluene, and after removal of the catalyst by using a membrane filter, an object was analyzed with High Performance Liquid Chromatography (HPLC) [wavelength: 236 nm, flow rate: 1 mL/min, mobile phase: a mixed solvent of water/acetonitrile/acetic acid/triethylamine (=600/400/1/1), measurement time: 60 min, and standard substance: toluene]. The results were as follows: Remaining rate of nitrobenzene (45.68%), formation rate of N-phenylhydroxylamine (99.17%), by-product rate of anilne (by-product) (0.45%), conversion rate of nitrobenzene (54.32%), and yield of N-phenylhydroxylamine (53.87%). These results are summarized altogether in Table 7.

Figure 8:
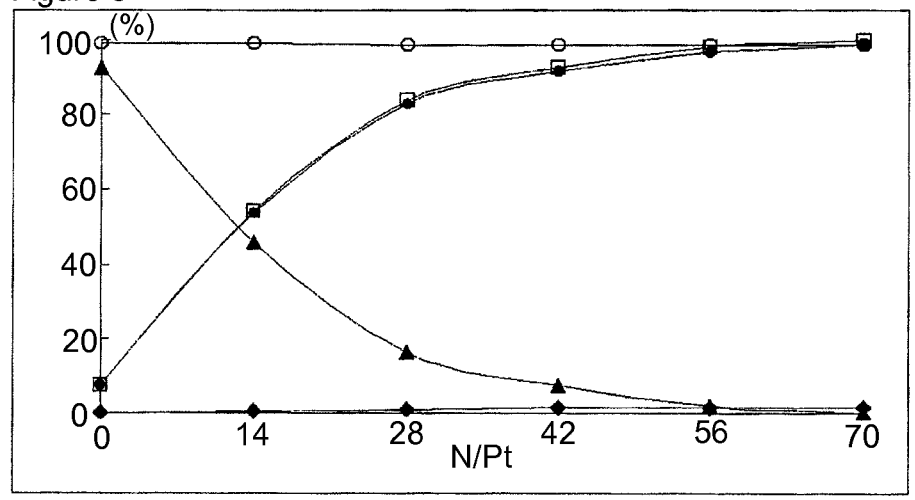
FIG. 8 shows remaining rate of nitorobenzene, formation rate of N-phenylhydroxylamine, by-product rate of aniline (a by-product), conversion rate of nitorobenzene, and yield of N-phenylhydroxylamine, obtained in Comparative Example 9 and Examples 44 to 48, relative to the addition quantity of triethylamine.

In addition, remaining rate of nitrobenzene, formation rate of N-phenylhydroxylamine, by-product rate of anilne (by-product), conversion rate of nitrobenzene, and yield of N-phenylhydroxylamine, relative to the addition quantity of triethylamine are summarized altogether in FIG. 8.

It should be noted that each line in FIG. 8 shows the following item:
—▲— line: remaining rate of nitrobenzene
—●— line: formation rate of N-phenylhydroxylamine,
—♦— line: by-product rate of aniline (by-product),
—□— line: conversion rate of nitrobenzene
—○— line: selectivity of N-phenylhydroxylamine Examples 45 to 48

Similar operation as in Examples 44 is performed, except that 20 µL, 30 µL, 40 µL, and 50 µL, (28 equivalents, 42 equivalents, 56 equivalents, and 70 equivalents, relative to platinum weight (N/Pt) in the silica gel platinum catalyst) of triethylamine were used, instead of 10 µL, to obtain an object. The results are summarized altogether in FIG. 8.

Comparative Example 9

Similar operation as in Example 44 is performed, except that triethylamine was not added, to obtain an object. The results are summarized altogether in FIG. 8.

Examples 49 to 53

A Method for Producing an Arylhydroxylamine Using a Platinum Catalyst Supported on Silica Into a flask, 20 mg of the silica gel platinum catalyst (5% by weight of Pt) [product name: 5% Pt-silica powder "Escat™ 2351", manufactured by STREM Co., Ltd.] (0.0026 time mole of platinum, relative to nitrobenzene), 2 mL of IPA (isopropyl alcohol), 0.42 mmol of dimethylsulfoxide (30 µL), 0.072 mmol of n-butylamine (7.1 µL) (14 equivalents, relative to platinum weight in the silica gel platinum catalyst) and 2 mmol of various nitroaryl compounds described in the following Table 5 were charged, and then a balloon sealed with hydrogen gas (about 2 L) was attached, and a reaction was carried out under stirring at room temperature for predetermined time under ordinary pressure. After completion of the reaction, 20 µL of the resultant reaction solution was diluted with 10 mL of 2-propanol containing 0.1 M of toluene, and after removal of the catalyst by using a membrane filter, IPA was removed under reduced pressure, and it was analyzed with NMR. The results are summarized in Table 5.

TABLE 5

| | Substrate | Reaction Time (minutes) | Conversion rate (%) | Yield (%) | Selectivity (%) |
|---|---|---|---|---|---|
| Example 49 | 4-chloronitrobenzene | 100 | 100 | 98 | 98 |
| Example 50 | 4-fluoronitrobenzene | 100 | 97 | 96 | 99 |
| Example 51 | nitrobenzene | 105 | 99 | 98 | 99 |
| Example 52 | 4-methylnitrobenzene | 180 | 99 | 97 | 98 |
| Example 53 | 4-methoxynitrobenzene | 300 | 99 | 96 | 97 |

Examples 54 to 61

Into a flask, 20 mg of the silica gel platinum catalyst (5% by weight of Pt) [product name: 5% Pt-silica powder "Escat™ 2351", manufactured by STREM Co., Ltd.] (0.0026 time mole of platinum, relative to nitrobenzene), 2 mL of IPA, 30 µL of dimethylsulfoxide, 0.072 mmol of various amines shown in the following Table 5 (14 equivalents, relative to platinum weight (N/Pt) in the silica gel platinum catalyst) and 2 mmol of nitrobenzene were charged, and then a balloon sealed with hydrogen gas (about 2 L) was attached, and a reaction was carried out under stirring at room temperature for 2 hours under ordinary pressure. After completion of the reaction, 20 µL of the resultant reaction solution was diluted with 10 mL of 2-propanol containing 0.1 M of toluene, and after removal of the platinum catalyst supported on amino group-coordinated silica by using a membrane filter, an object was analyzed with High Performance Liquid Chromatography (HPLC) [wavelength: 236 nm, flow rate: 1 mL/min, mobile phase: a mixed solvent of water/acetonitrile/acetic acid/triethylamine (=600/400/1/1), measurement time: 60 min, and standard substance: toluene]. These results are summarized altogether in Table 6.

Comparative Example 10

Similar operation as in Example 54 is performed, except that the amine was not added, to obtain an object. The results are summarized in Table 6.

TABLE 6

| | Various amines | | Conversion Rate (%) | Yield (%) | Selectivity (%) |
|---|---|---|---|---|---|
| Example 54 | sec-butylamine (sec-BuNH$_2$): | Primary amine | 85.5 | 84.7 | 99.0 |
| Example 55 | Benzylamine (PhCH$_2$NH$_2$) | | 83.0 | 82.4 | 99.4 |
| Example 56 | n-butylamine (n-BuNH$_2$) | | 78.3 | 77.5 | 99.0 |
| Example 57 | piperidine | Secondary amine | 71.5 | 71.0 | 99.2 |
| Example 58 | Diethylamine (Et$_2$NH) | | 50.0 | 49.8 | 99.5 |
| Example 59 | Diisopropylamine (iso-Pr$_2$NH) | | 33.0 | 32.8 | 99.6 |
| Example 60 | Triethylamine (Et$_3$N) | Tertiary amine | 26.5 | 26.3 | 99.3 |
| Example 61 | tetramethylethylenediamine (TMEDA) | Diamines | 68.3 | 68.0 | 99.6 |
| Compar. Exam. 10 | non-addition | — | 4.1 | 4.0 | 97.6 |

Reference Example 14

Synthesis of a Platinum Catalyst Supported on Silica

Onto 3.27 g of mesoporous silica synthesized by a common procedure (for example, D. Zhao, et. al., Science 279, p 548 (1998) or the like), 20.0 mL of an aqueous solution containing $4.4 \times 10^{-2}$ M of H$_2$PtCl$_6$ hexahydrate was dropped, and after standing still at room temperature for 2 hours, the solution was subjected to drying under vacuum at 60° C. for 1.5 hour. Still more, the resultant dried substance was calcinated at 500° C. for 4 hours to obtain 2.81 g of the platinum catalyst supported on mesoporous silica. Quantity of platinum supported on the resultant platinum catalyst supported on mesoporous silica was found to be about 5% by weight, by calculation result from total platinum quantity used.

[Property Data]

Specific surface area; 636 m$^2$/g pore volume; 0.48 cm$^3$/g

Example 62

A Method for Producing an Arylhydroxylamine Using a Platinum Catalyst Supported on Silica Into a 25-mL flask, 20 mg of the platinum catalyst supported on silica (hereafter may be abbreviated as "platinum catalyst supported on mesoporous silica") (0.0026 time mole of platinum, relative to nitrobenzene) obtained in Reference Example 14, 2 mL of isopropyl alcohol (IPA), 30 µl, of dimethylsulfoxide, 2 mmol of nitrobenzene and 10 µL of triethylamine (14 equivalents, relative to platinum weight in the platinum catalyst supported on silica (N/Pt)) were charged, and then a balloon sealed with hydrogen gas (about 2 L) was attached, and a reaction was carried out under stirring at room temperature for 2 hours under ordinary pressure. After completion of the reaction, 20 µL of the resultant reaction solution was diluted with 10 mL of 2-propanol containing 0.1 M of toluene, and after removal of the platinum catalyst supported on amino group-coordinated silica by using a membrane filter, an object was analyzed with High Performance Liquid Chromatography (HPLC) [wavelength: 236 nm, flow rate: 1 mL/min, mobile phase: a mixed solvent of water/acetonitrile/acetic acid/triethylamine (=600/400/1/1), measurement time: 60 min, and standard substance: toluene], and, as a result, conversion rate of nitrobenzene was 79.22% and yield of N-phenylhydroxylamine was 73.93% (selectivity 93.32%). The results are shown in Table 7.

Example 63

A Method for Producing a Hydroxylamine Using the Platinum Catalyst Supported on Amino Group-Coordinated Silica Relevant to the Present Invention Similar operation as in Example 62 is performed, except that the platinum catalyst supported on amino group-coordinated silica (hereafter may be abbreviated as "platinum catalyst supported on amino group-coordinated mesoporous silica") obtained in Reference Example 13 was used, instead of the platinum catalyst supported on silica obtained in Reference Example 14, the triethylamine was not added, and 120 μL of dimethylsulfoxide was used, to obtain an object. The results are summarized altogether in Table 7.

Comparative Example 11

Similar operation as in Example 62 is performed, except that the triethylamine was not added, to obtain an object. The results are summarized in Table 7.

TABLE 7

| | Silica | Amine | DMSO (μL) | Reaction Time (h) | Conversion Rate (%) | Yield (%) | Selectivity (%) |
|---|---|---|---|---|---|---|---|
| Exam. 44 | Silica gel Pt cat. | Trienhyl amine | 30 | 2 | 54.32 | 53.87 | 99.17 |
| Exam. 62 | mesoporous silica Pt cat. | Trierhyl amine | 30 | 2 | 79.22 | 73.93 | 93.32 |
| Exam. 63 | amino group-coordinated mesoporous silica Pt cat. | Non | 120 | 2 | 100 | 94.31 | 94.31 |
| Compar. Exam. 11 | mesoporous silica Pt cat. | Non | 30 | 2 | 5.79 | 5.31 | 91.71 |

As is clear from Table 1, it has been confirmed that by reacting the nitroaryl compound represented by the general formula [4] with hydrogen gas (hydrogen source), using the platinum catalyst supported on amino group-coordinated silica relevant to the present invention, an objective arylhydroxylamine compound may be produced efficiently under mild reaction conditions, by using an inexpensive hydrogen source (hydrogen gas), without having the conventional problems that a reaction must be carried out, for example, under severe condition such as reflux condition, or an expensive hydrogen source (for example, hydrazine or the like) must be used.

In addition, as is clear from the results of Table 2, an objective arylhydroxylamine compound may be obtained also by using various platinum catalysts supported on amino group-coordinated silica relevant to the present invention.

Still more, as is clear from the results of Table 3, an object may be obtained efficiently also by using various reaction solvents.

As is clear from the results of Comparative Examples 1 and 2, it has been found that an object was not obtained efficiently when dimethylsulfoxide (a catalyst poisoning agent) was not added, even in the case where the platinum catalyst supported on amino group-coordinated silica relevant to the present invention was used.

As is clear from the results of Comparative Example 3, in the case of using a commercially available silica gel platinum catalyst, if an amine compound is not added, although dimethylsulfoxide (poisoning agent) is added, an object is not obtained efficiently. In addition, it has been found that a reaction time of 20 hours, as compared with a reaction time of 2 hours, enhances conversion rate of nitrobenzene, however, because of decrease in selectivity of the objective N-phenylhydroxylamine, results in to by-produce a large quantity of aniline.

As is clear from the results of Comparative Examples 3 to 6, it has been found that, in the case of using a commercially available silica gel platinum catalyst, that is, in the case of using a silica platinum catalyst that amino group is not introduced, when dimethylsulfoxide (a poisoning agent) and an amine compound are not added, the objective N-phenylhydroxylamine is not formed efficiently (Comparative Example 5). In addition, it has been found that an object was not formed efficiently, similarly, also when either of the poisoning agent or the amine compound was added (Comparative Examples 3, 4 and 6).

Still more, as is clear from the results of Comparative Example 4, it has been found that the object was not formed efficiently, even in the case where mesoporous silica was used as silica (a carrier), when the amine compound is not added, or an amino group is not introduced onto the relevant mesoporous silica.

As is clear from the results of Comparative Examples 5 to 6, and FIGS. 1 to 2, it has been found that selectivity of the objective N-phenylhydroxylamine is low, that is, aniline is by-produced, irrespective of presence or absence of the amine compound, in the case where dimethylsulfoxide (DMSO), which is a poisoning agent, is not added.

As is clear from the results of Examples 34 to 37, Comparative Example 7, and FIGS. 3 to 4, it has been found that increase in the addition quantity (N/Pt) of the amine compound relative to platinum quantity in the catalyst, in the coexistence of a poisoning agent, enhances conversion rate of nitrobenzene, yield and selectivity of N-phenylhydroxylamine.

In addition, as is clear from the results of FIGS. 4 to 5, it has been found that increase in catalyst quantity to be used enhances conversion rate of nitrobenzene and yield of N-phenylhydroxylamine. In addition, in the case where the addition quantity (N/Pt) of triethylamine relative to platinum weight in the catalyst is 6 equivalents, it has been found to provide N-phenylhydroxylamine in high yield and in high purity.

As is clear from the results of Examples 40 to 41, and Table 4, it has been found that increase in catalyst quantity, and increase in the addition quantity (N/Pt) of triethylamine relative to platinum weight in the catalyst enhance selectivity of N-phenylhydroxylamine, and in addition, an object is formed efficiently in a short reaction time.

As is clear from the results of Examples 42 to 43, and FIGS. 6 to 7, it has been found that, in the case where mesoporous silica is used as silica in the platinum catalyst supported on amino group-coordinated silica relevant to the present invention, an objective N-phenylhydroxylamine, is formed efficiently in a short time (30 minutes).

As is clear from the results of FIGS. 4 and 6, and FIGS. 5 and 7, it has been found that, in the case where mesoporous silica is used (FIGS. 7 and 7), as compared with case where usual silica gel is used (FIGS. 4 and 5), as silica in the platinum catalyst supported on amino group-coordinated silica relevant to the present invention, an objective N-phenylhydroxylamine is formed more efficiently in a short time.

As is clear from the results of FIGS. 4 to 5, and FIGS. 6 to 7, it has been found that, increase in platinum weight in the catalyst relevant to the present invention, enhances reaction efficiency, that is, generates an object, efficiently in a short reaction time.

As is clear from the results of Table 5, it has been found that, also in the case where various nitroaryl compounds are used as substrates, an objective N-phenylhydroxylamine is formed efficiently (Examples 49 to 53).

As is clear from the results of Table 6, it has been found that, in the case where various kinds of amine compounds are added to a reaction relevant to the present invention, the primary amine compounds (Examples 54 to 56), the secondary amine compounds (Examples 57 to 59), and the tertiary amine compounds (Example 60), in this order, exhibit high values of yield and selectivity of the resultant N-phenylhydroxylamine, along with conversion rate of nitrobenzene. In addition, it has been found that diamines also show similar results.

As is clear from the results of Table 7, it has been found that, in the case where mesoporous silica is used, as a carrier of the platinum catalyst supported on silica relevant to the present invention, yield and selectivity of N-phenylhydroxylamine increases, as compared with use of silica gel as a carrier thereof (Examples 44 and 62). In addition, it has been found that use of the platinum catalyst supported on amino group-coordinated mesoporous silica (Example 63) provides higher yield and selectivity of N-phenylhydroxylamine, as compared with use of one where an amine compound was added to the platinum catalyst supported on mesoporous silica (Example 62). Dimethylsulfoxide (poisoning agent) acts so as to suppress the catalytic activity, however, results of Example 63, as compared with results of Example 62, enables to provide an object in higher conversion rate, yield and selectivity, although usage of dimethylsulfoxide in Example 63 is 4 times that in Example 62. This fact shows that the platinum catalyst supported on amino group-coordinated mesoporous silica is a preferable catalyst in formation of an objective arylhydroxylamine compound.

INDUSTRIAL APPLICABILITY

According to the method of the present invention, where a nitroaryl compound are contacted with a hydrogen source in the coexistence of a platinum catalyst supported on amino group-introduced silica and a poisoning agent, an objective arylhydroxylamine compound may be produced efficiently, industrially and safely under mild conditions, without having problems that a reaction must be carried out, for example, under severe condition such as reflux condition and an expensive hydrogen source (for example, hydrazine or the like) is required or the like, which a conventional method had.

The invention claimed is:

1. A method for producing an arylhydroxylamine compound, which comprises contacting a nitroaryl compound with a hydrogen source in the presence of a platinum catalyst supported on amino group-coordinated silica and a poisoning agent.

2. The method according to claim 1, which is carried out under 0.1 to 1 MPa.

3. The method according to claim 1, wherein the silica has a specific surface area of 10 $m^2/g$ to 2000 $m^2/g$.

4. The method according to claim 1, which is carried out at −80 to 100° C.

5. The method according to claim 1, wherein the hydrogen source is hydrogen gas.

6. The method according to claim 1, wherein the poisoning agent is a compound comprising an atom having an unshared electron pair selected from an oxygen atom, a phosphorous atom and a sulfur atom.

7. The method according to claim 1, wherein the amino group is selected from a primary amino group, a secondary amino group, a tertiary amino group and a quaternary ammonium group.

8. The method according to claim 7, wherein the amino group is a primary amino group.

9. The method according to claim 1, wherein the platinum catalyst supported on amino group-coordinated silica is obtained by supporting a platinum on silica, which the amino group is introduced.

10. The method according to claim 1, wherein the platinum catalyst supported on amino group-coordinated silica is obtained by contacting the platinum catalyst supported on silica with an amine compound.

11. The method according to claim 1, wherein the platinum catalyst supported on amino group-coordinated silica is obtained by supporting an amine compound and a platinum on silica, at the same time.

* * * * *